(12) United States Patent
Janik et al.

(10) Patent No.: US 8,781,600 B2
(45) Date of Patent: Jul. 15, 2014

(54) IMPLANTABLE ELECTRODE ARRAY ASSEMBLY INCLUDING A CARRIER IN WHICH CONTROL MODULES FOR REGULATING THE OPERATION OF THE ELECTRODES ARE DISPOSED AND ELECTRODES THAT ARE DISPOSED ON TOP OF THE CARRIER

(75) Inventors: John Janik, Hudsonville, MI (US); Rob Brindley, Delton, MI (US); Rakesh Babu Katragadda, Ann Arbor, MI (US); Edward Chia-Ning Tang, Ann Arbor, MI (US)

(73) Assignee: Stryker Corporation, Kalamazoo, MI (US)

( * ) Notice: Subject to any disclaimer, the term of this patent is extended or adjusted under 35 U.S.C. 154(b) by 1304 days.

(21) Appl. No.: 12/535,717

(22) Filed: Aug. 5, 2009

(65) Prior Publication Data

US 2011/0034977 A1 Feb. 10, 2011

(51) Int. Cl.
*A61N 1/00* (2006.01)

(52) U.S. Cl.
USPC .............. 607/116; 607/117; 607/41; 607/46; 607/48

(58) Field of Classification Search
USPC ........................... 600/377; 607/116, 117, 148
See application file for complete search history.

(56) References Cited

U.S. PATENT DOCUMENTS

| | | | |
|---|---|---|---|
| 6,304,784 B1 * | 10/2001 | Allee et al. | 607/116 |
| 2006/0287660 A1 | 12/2006 | Syed et al. | |
| 2008/0288037 A1 | 11/2008 | Neysmith et al. | |
| 2009/0124965 A1 | 5/2009 | Greenberg et al. | |
| 2011/0077660 A1 | 3/2011 | Janik et al. | |
| 2012/0022551 A1 | 1/2012 | Staunton et al. | |

FOREIGN PATENT DOCUMENTS

| | | |
|---|---|---|
| EP | 1 883 107 A2 | 1/2008 |
| WO | 2008/080073 A2 | 7/2008 |

OTHER PUBLICATIONS

Bulcke, et al., "Active Electrode Arrays ByChip Embedding in a Flexible Silicone Carrier, 28th IEEE EMBS Annual International Conference", Aug. 2006.
European Patent Office, "Partial Search Report for PCT/US2010/044401," Feb. 2011.
European Patent Office, "ISA Search Report and Written Opinion for PCT App. No. PCT/US2010/044401", Aug. 29, 2011.

* cited by examiner

*Primary Examiner* — Mark W Bockelman

(57) ABSTRACT

An implantable electrode array that includes multiple spaced apart electrodes to which current can be individually sourced and sunk. The array includes a carrier that supports the electrodes. One or more control modules that source current to or sink current from the electrodes are disposed in recesses within the carrier. A sheet of material more flexible than the carrier is disposed between, on one side, the carrier and the control modules and, on the other side, the electrodes. Conductors over which instructions and power are applied to the control modules and conductors that extend between the control modules are the electrodes are embedded in and extend through the sheet of flexible material.

23 Claims, 42 Drawing Sheets

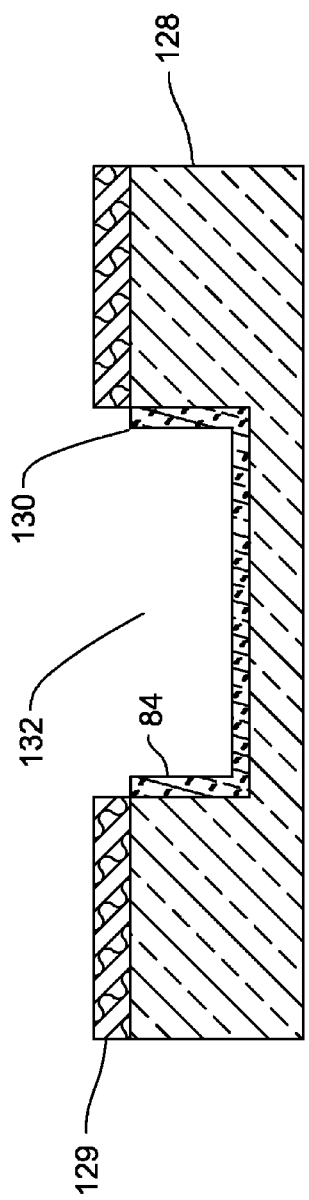
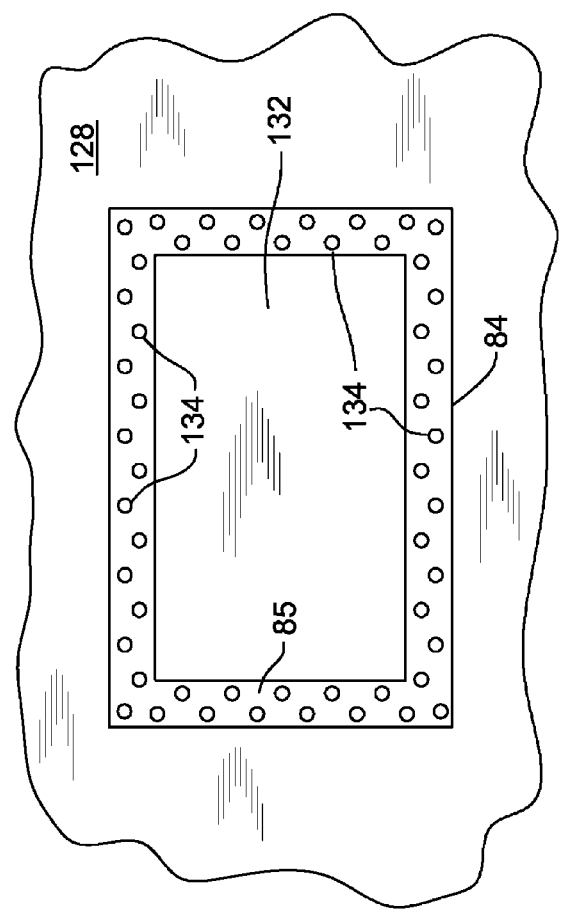

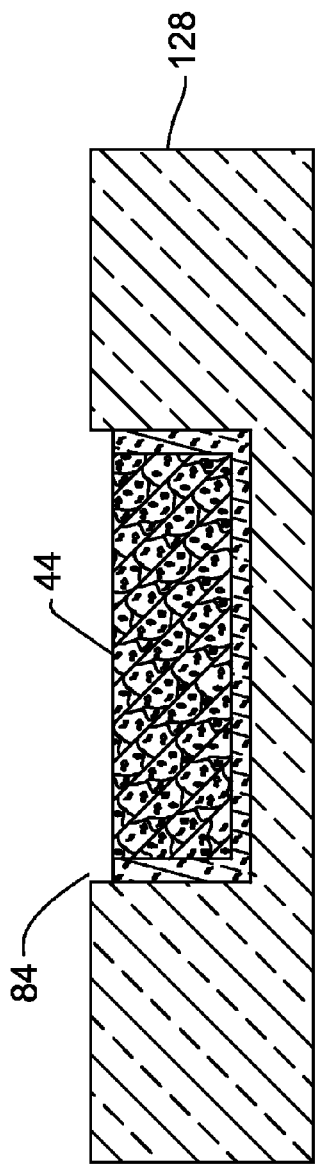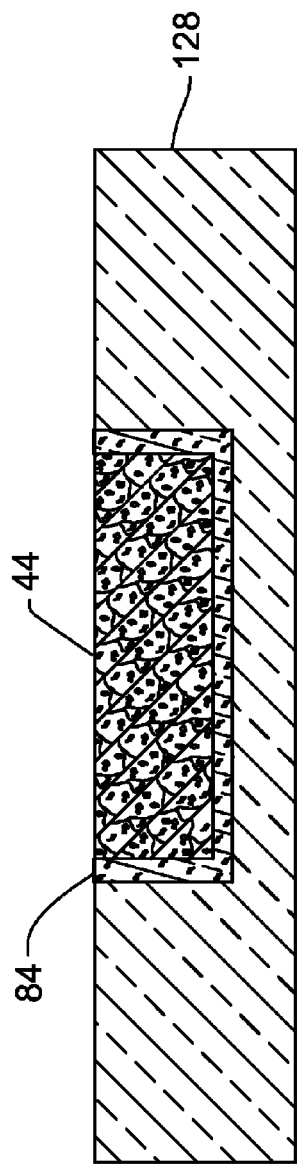

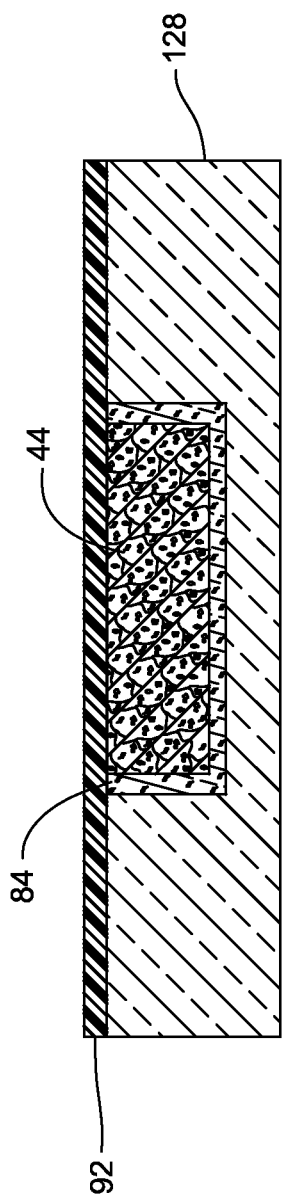
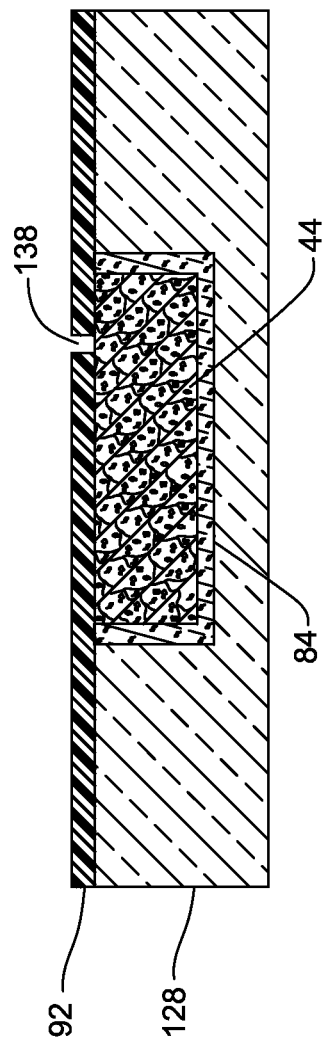

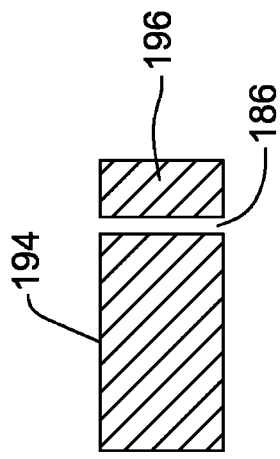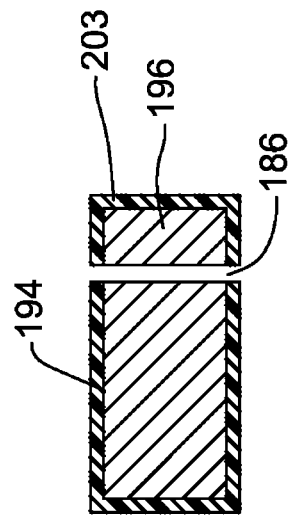
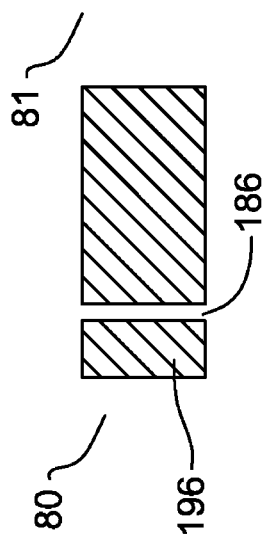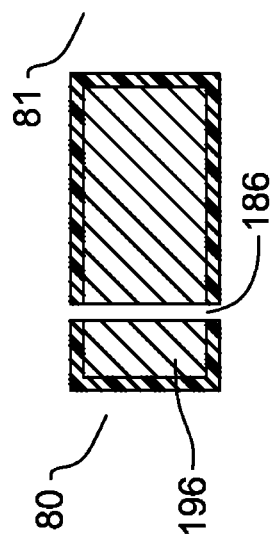
FIG. 27    FIG. 28

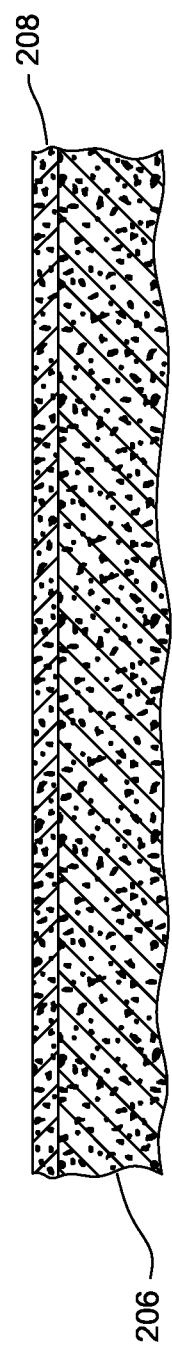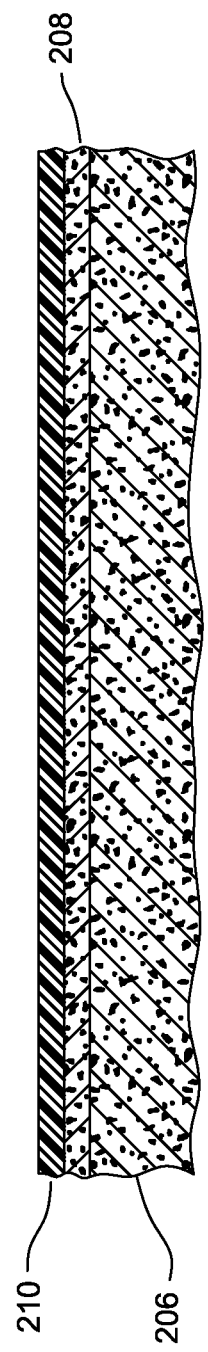

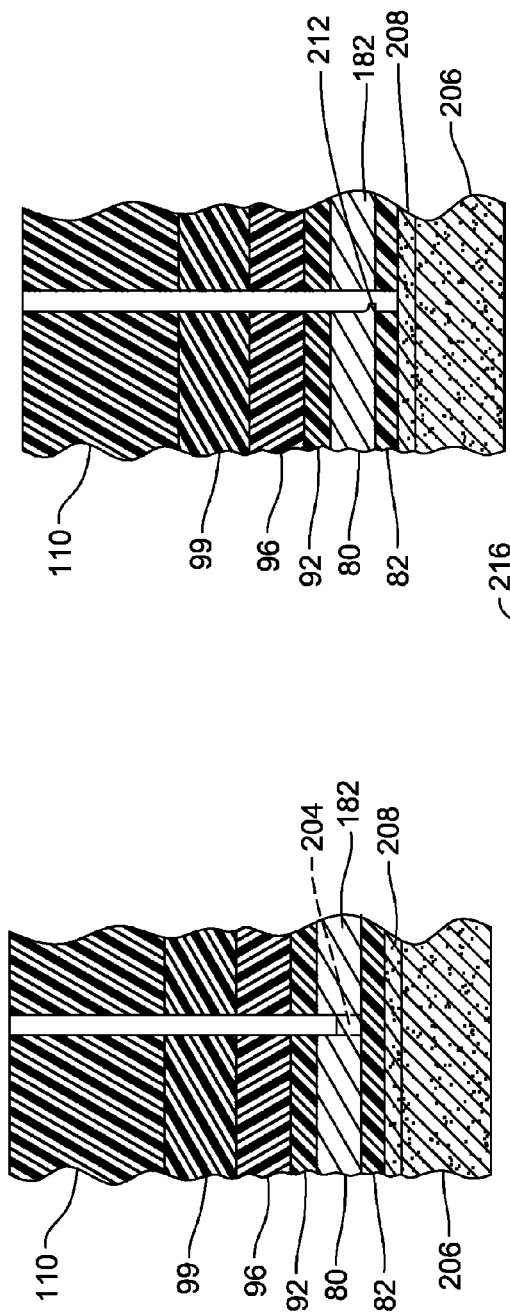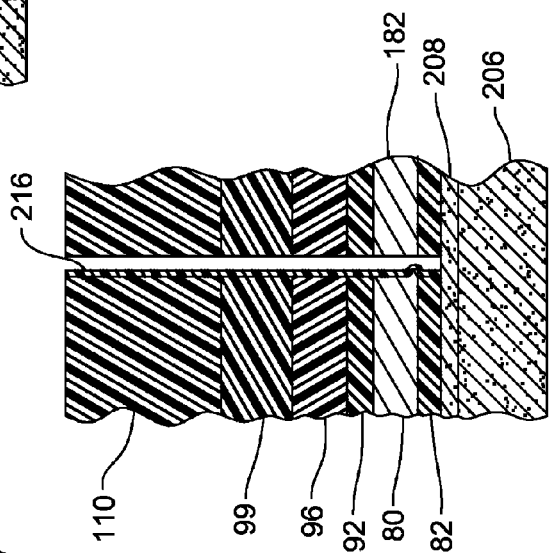

IMPLANTABLE ELECTRODE ARRAY ASSEMBLY INCLUDING A CARRIER IN WHICH CONTROL MODULES FOR REGULATING THE OPERATION OF THE ELECTRODES ARE DISPOSED AND ELECTRODES THAT ARE DISPOSED ON TOP OF THE CARRIER

FIELD OF THE INVENTION

This invention relates generally to an implantable electrode array assembly and, more particularly, to an implantable electrode array assembly with one or more control modules for regulating the operation of the assembly embedded in the carrier that supports the electrodes.

FIELD OF THE INVENTION

There are a number of medical conditions for which it has been found that an effective therapy involves driving current through a section of the tissue of a patient. Often, the current is driven between the electrodes of an electrode array implanted in the patient. Generally, the electrode array includes a non-conductive carrier on which typically two or more electrodes are disposed. Once the electrode array is implanted, current is driven from at least one of the electrodes, through the adjacent tissue, to at least one of the other electrodes. The current flow through the tissue influences the tissue to accomplish a desired therapeutic result. For example, an electrode array positioned adjacent the heart may flow currents to stimulate the appropriate contraction and expansion of the heart muscles.

There is an increasing interest in implanting electrode arrays adjacent neural tissue so that the resultant current flow induces a desired neurological or physical effect. In one known application, the current driven between the electrodes of an array placed on top of the dura in the vertebral column reduces the extent to which chronic pain signals are perceived by the brain. Alternatively, the array may be placed in a location where the current flow stimulates a feeling of satiation as part of an appetite suppression/weight management therapy. In another application, the current is flowed to tissue or nerves associated with the bladder or the anal sphincter to assist in control of incontinence. Electrodes may be implanted in a paralysis victim to provide muscle control and/or a sense of feeling.

The Applicants' Patent Application No. PCT/US2009/33769, FOLDABLE, IMPLANTABLE ELECTRODE ARRAY ASSEMBLY AND TOOL FOR IMPLANTING SAME, filed 11 Feb. 2009, published as U.S. Pat. Pub. No. 2011/0077660A1, the contents of which are explicitly incorporated herein by reference, describes an electrode array that includes a carrier on which plural electrodes are arranged in a row by column matrix. An advantage of this electrode array is that it allows current to be flowed between numerous different combinations of electrodes. Depending on which electrodes are connected to associated current sources and sinks, this array can be operated so that there are two or more current flows occurring simultaneously between different sets of electrodes. Once this assembly is deployed, the practitioner can initially drive current between different combinations of electrodes. Current therefore flows through different sections of tissue. This allows the practitioner to determine between which electrodes, through which tissue, the current flow offers the greatest benefit and/or tolerable side effects. Once the optimal current flow path between the electrodes is determined, the array and its associated power supply are set to operate in this state.

In comparison to other electrode arrays with lesser numbers of electrodes, the above-described array makes it possible to flow current through more sections of tissue and to selectively focus/diffuse the current flow. In contrast to an electrode array with a smaller number of electrodes, use of the above-described array increases the likelihood that the current flow can be set to provide desired therapeutic effects, with tolerable side effects.

Still another advantage of the above-described array is that the carrier is formed from superelastic material. A superelastic material is one that, after being subjected to appreciable bending or folding, returns to its initial state. Thus, once this electrode array is formed, the assembly is then folded or rolled into a form that has a side-to-side width appreciably less than its width in the unfolded/unrolled state. A benefit of an electrode array assembly of this design is that it can be folded into a sheath. The sheath-encased electrode array assembly can then be inserted through an access cannula using a minimally invasive procedure into the patient. Once in the patient, the sheath and assembly are steered to over the tissue against which the electrodes integral with the assembly are deployed. Once the assembly is properly positioned, the sheath is opened up or removed. The opening/removal of the sheath causes the carrier to unfold. As a consequence of the carrier unfolding, the electrodes deploy over the target tissue. A more complete understanding of how the electrode array assembly can be so positioned and deployed is contained in the Applicants' Assignee's U.S. Pat. App. No. 61/166,366, DELIVERY ASSEMBLY FOR PERCUTANEOUSLY DELIVERING AN ELECTRODE ARRAY AT A TARGET LOCATION, THE ASSEMBLY CAPABLE OF STEERING THE ELECTRODE ARRAY TO THE TARGET LOCATION, filed 3 Apr. 2009, which is incorporated herein by reference the contents of which are published in U.S. Pat. Pub. No. US 2012/0022551 A1.

Thus, not only does an electrode array built on a superelastic carrier provide a means for selectively flowing current through different sections of tissue, the assembly can be placed over the target tissue without having to cut a large incision in the patient.

One feature of the above-described array is that also mounted to the carrier are one or more drive modules. The drive modules contain the components that source/sink the current to/from the electrodes. It is necessary to provide some on array control circuitry because the array typically includes 10 or more and often 20 or more electrodes each of which serve as a current source and/or sink. Without providing these modules, it would be necessary to implant a large number of conductors that extend from the pulse generator, through the patient, over which the current is sourced/sunk to the individual electrodes. Physical constraints make it difficult to implant large numbers of conductors in the patient. The above referenced applications described how an electrode array may be constructed so that the drive module is disposed on the surface of the array on which the electrodes are disposed; the surface of the assembly disposed against the tissue. Alternatively, the drive module may be positioned on the surface of the carrier opposite the surface that faces the tissue.

Regardless of the location on the surface of the carrier on which the drive module is located, it is necessary to encase the module in some sort of package. The package protects the semi-conductor die forming the drive module. Often the package includes a shell and a cap. The shell surrounds one end and the sides of the die. The cap covers the exposed end of the array and the perimeter of the shell. Consequently, the known assemblies have some sort of conductors that extend from the electrodes, through the package to the semiconductor die. As mentioned above, a significant feature of the known assembly is that the carrier has some degree of flexibility. Accordingly, the conductors disposed on the carrier of this assembly are subjected to some flexing. Inside the package, the conductors are held rigid. Accordingly around the perimeter of the package, where the conductors are stopped from flexing, the conductors may be subjected to considerable stress. There is a concern that this stress could induce failure in the conductors.

Moreover, inside the package, wire bonds may have to be used to establish the final connections between the conductors and the complementary bond pads on the control module-forming semiconductor die. These wire bonds, given the fragility of the wires from which they are formed, may also be prone to breakage. In regard to this matter is should be appreciated that once electrode array assembly is implanted, the assembly, like the patient in which it is implanted, is almost always moving. Over time, the vibration induced by this movement can potentially cause these wire bonds to fracture. Clearly, the failure of these wire bonds, or complementary conductors can result in malfunction of electrode array.

SUMMARY OF THE INVENTION

This invention is related to a new and useful electrode array designed for implantation into a living being. The electrode array of this invention includes one or more control modules that are built into the array so as to minimize the extent to which the conductors that extend to the module/modules are subjected to breakage-inducing stress.

The electrode array of this invention includes a carrier. Typically the carrier is formed out of material that is at least flexible so that the carrier at least conforms to the tissue against which the array is deployed. Often the carrier is formed from material that, in addition to being flexible, has some degree of elasticity. This allows the electrode array assembly to be deployed using minimally invasive surgical techniques.

The electrode array of this invention also includes one or more control modules. A control module is a semiconductor die. The components fabricated on the control module source/sink current to one or more of the electrodes. Each control module is seated in a window or a recess formed in carrier. In many versions of the invention, a layer of biocompatible material surrounds one or more of the exposed faces of the control module to serve as a partial package around the module. Insulating material that has some degree of flexibility is disposed over the exposed surfaces of the carrier and adjacent exposed surfaces of the module/modules. Vias extend through the insulating material to complementary bond pads on the control module/modules. Some of the vias extend to the individual electrodes. Other ones of the vias extend to conductors also part of the array. These conductors, and the vias to which they are connected, function as the conductive members through which power and/or operating instructions that originate off the array are applied to the control module/modules.

In some versions of the invention, a control module is associated with each electrode. The control module may be seated in a window or other opening in the carrier so as to be below the electrode.

The vias and conductors of the electrode array of this invention are primarily disposed on or extend through layers of material that has some degree of flexibility. The vias themselves are relatively short in length. The conductors to which the vias extend are thin both in their height and width. These dimensional features of the vias and on-array conductors improve their flexibility. Collectively, the flexibility of these components, the insulating material, the vias and the conductors, reduces the extent to which the mechanical stress to which the vias and conductors are exposed can cause their breakage.

BRIEF DESCRIPTION OF THE DRAWINGS

The invention is pointed out with particularity in the claims. The above and further features and advantages of this invention are better understood from the below Detailed Description taken in conjunction with the accompanying drawings in which:

FIGS. 5 and 6 are cross sectional view depicting initial steps of the fabrication of an electrode array assembly on a support substrate;

FIG. 7 is a top plan view of a partially fabricated control module shell of the electrode array assembly;

FIGS. 8-25 are a sequence of cross sectional views depicting the fabrication how an electrode and associated control module of an electrode array are, according to this invention, fabricated on a wafer;

FIGS. 27 and 28 are cross sectional views depicting how the carrier is prepared for bonding to a substrate;

FIGS. 29 and 30 are cross sectional views depicting how the substrate is prepared to receive the carrier;

FIGS. 34-36 are cross sectional views depicting the steps executed to separate the electrode array carrier from the adjacent section of the coupon to which the carrier was connected;

DETAILED DESCRIPTION

I. Electrode Array Assembly

Figure 1:
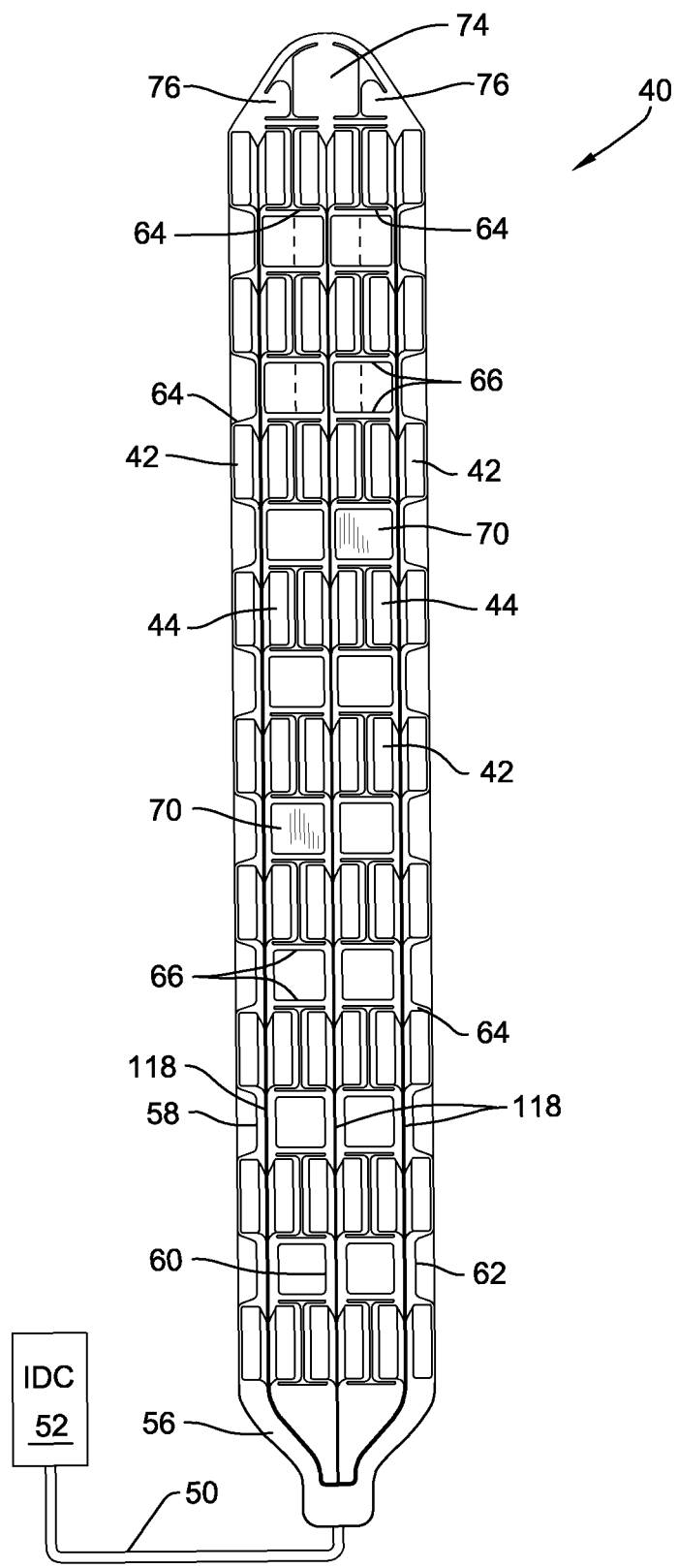
FIG. 1 is plan view of an electrode array assembly of this invention.
Figure 1A:
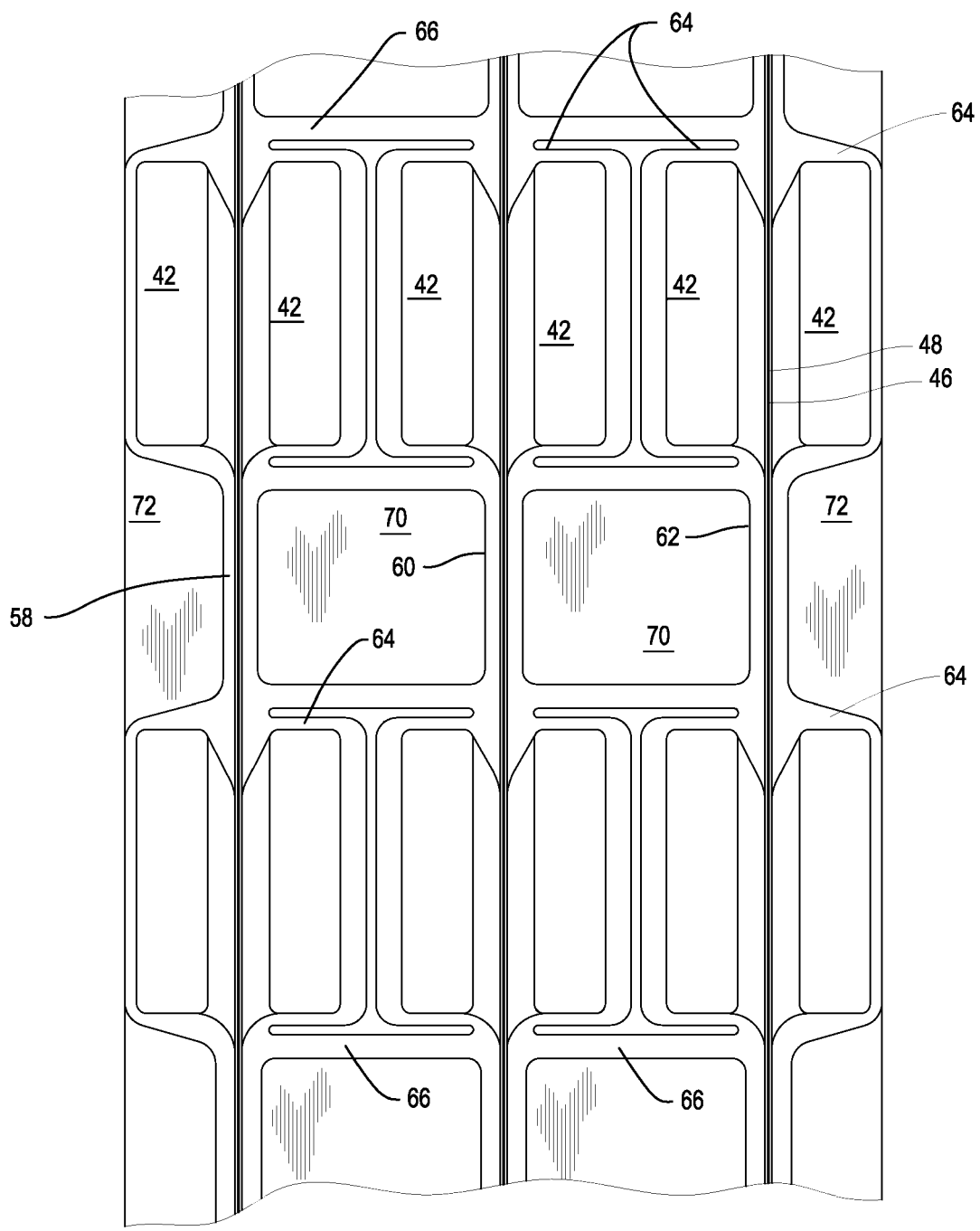
FIG. 1A is an enlarged view of a section of the electrode array of FIG. 1.
Figure 2:
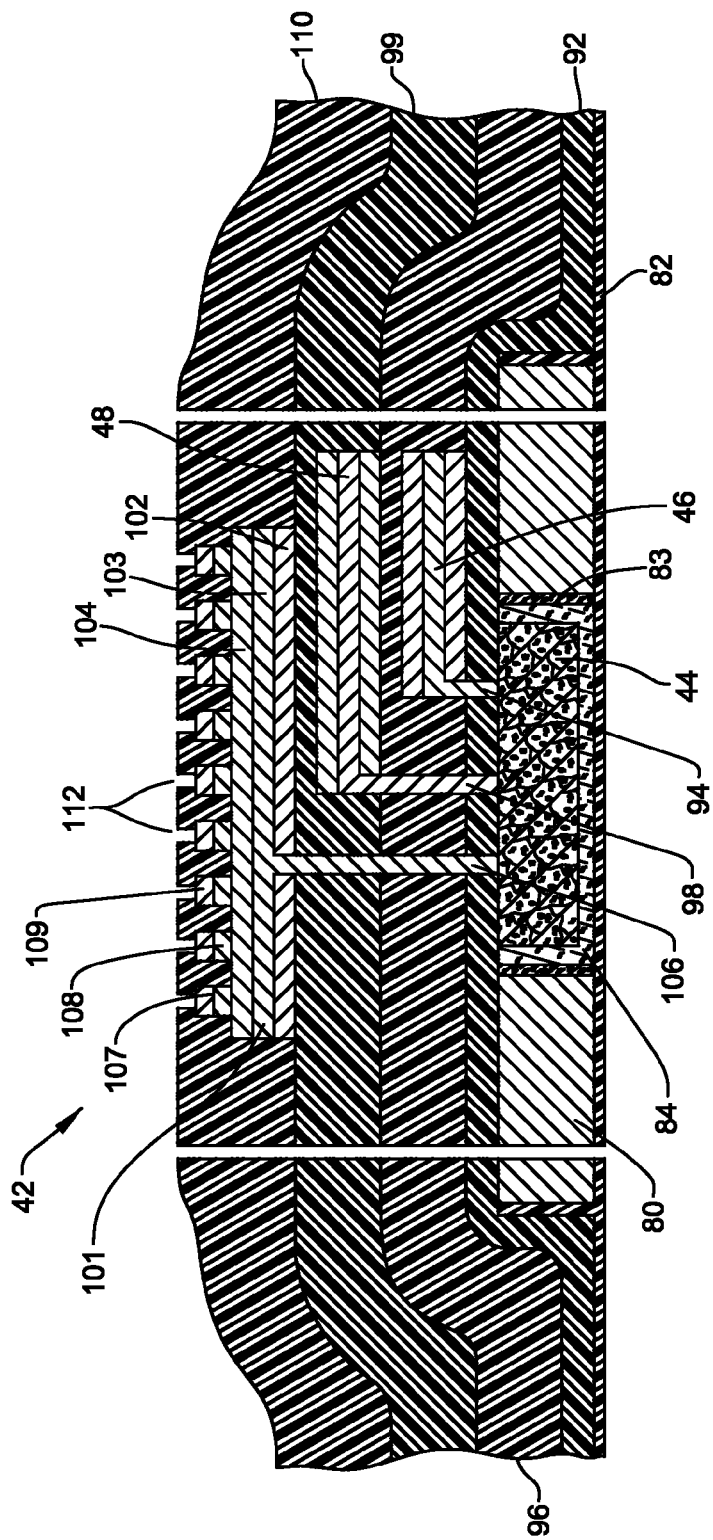
FIG. 2 is a cross sectional view of a portion of the electrode array assembly showing a single electrode and the control module associated with that electrode.

FIGS. 1, 1A and 2 illustrate an electrode array 40 of this invention. Electrode array 40 includes a number of individual electrodes 42 depicted in outline as a number of rectangles in FIGS. 1 and 1A. Associated with each electrode 42 is a control module 44. Each control module 44 is an application specific integrated circuit (ASIC) that includes components able to source current from/sink current to the associated electrode 42. Conductors 46 and 48 extend from the control modules 44. Conductors 46 and 48 are connected to a cable 50 that extends from the proximal end of the electrode array assembly 40. Not illustrated are the individual conductors internal to cable 50. Cable 50 is connected to an implantable device controller (IDC) 52. The IDC contains the power source for the currents that are flowed between the electrodes 42. IDC 52 also contains a controller that generates the instructions that indicate between which electrodes 42 the currents are to be flowed. The specific structure of the IDC 52 is not part of the present invention.

Electrode array assembly 40 is shaped to have a base 56 that is the most proximal portion of the assembly. (Here, "proximal" means towards the end of the assembly at the bottom of FIG. 1; "distal" means towards the end of the assembly at the top of FIG. 1). Three parallel, spaced apart bridges 58, 60 and 62 extend distally forward from base 56. The outer two bridges, bridges 58 and 62, extend forward from the opposed sides of base 56.

Plural tabs 64 extend outwardly from each bridge 58, 60 and 62. More particularly, at a number of spaced apart locations along the length of each bridge 58, 60 and 62, two tabs 64 extend outwardly from the opposed sides of the bridge. At least in the version of the invention depicted in FIGS. 1 and 1A, the tabs 64 are arranged in diametrically opposed pairs relative to the bridge 58, 60 or 62, from which the individual tabs extend. Electrode array assembly 40 is further constructed so that at each longitudinal section on bridge 58 from which tabs extend, tabs 64 also extend from the laterally adjacent longitudinal sections of bridges 60 and 62. Thus, in the illustrated version of the invention, tabs 64 are arranged in rows. In each row of tabs 64, two tabs extend outwardly from each bridge 58, 60 and 62. The rows of tabs 64 are longitudinally spaced apart from each other. In some versions of the invention, the separation between the distal end of one row of tabs and the proximal end of the distally adjacent row of tabs is between 1 to 10 mm. In many versions of the invention, this separation is between 2 and 6 mm.

Each tab 64 is generally in the form of a rectangle with rounded corners. Each tab 64 has a length (measurement along an axis parallel to the longitudinal axis of assembly 40) of between 0.5 to 5 mm. Often this length is between 2 and 4 mm. Each tab 64 has a width, (measurement along the axis perpendicular to the longitudinal axis of assembly 40 in the plane of FIG. 2) of 0.25 to 2 mm. In many versions of the invention, this width is between 0.5 to 1 mm. It should further be understood that each tab 64 attached to one bridge 58 or 60 is separate from the adjacent tab 64 attached to the adjacent bridge 60 or 62. The spacing between the adjacent tabs 64 extending from adjacent bridges is typically no more than 500 microns and preferably 100 microns or less. This small separation between adjacent tabs 64 reduces the amount of tissue that can grow between the tabs. If appreciable tissue were allowed to grow between the tabs 64, this tissue could inhibit later removal of the assembly 40.

Beams 66 extend between the bridges 58, 60, and 62. More particularly, each beam 66 extends between adjacent bridges 58 and 60 or between adjacent bridges 60 and 62. In the illustrated version of the invention, assembly 40 is further constructed so that each beam 66 connecting bridges 58 and 60 is collinear with an adjacent beam connecting bridges 60 and 62. Each beam 66 has a width, (measurement along an axis parallel to the longitudinal axis of the assembly 40) of approximately 0.25 mm.

The electrode array assembly 40 of FIG. 1 is further constructed so that there is a pair of collinear beams 66 adjacent the proximal and distal ends of each of the tabs 64 in each row of tabs. Thus, in the illustrated version of the invention 16 pairs of beams connected the spaced apart bridges 58, 60, and 62 together.

Given the spacing between the tabs 64, it should be appreciated that the longitudinally adjacent pairs of beams 66 are spaced apart from each other along the longitudinal axis of electrode array assembly 40. As discussed below, a flexible membrane 70 is disposed between these adjacent spaced apart beams 66. In FIG. 1A some membranes 70 are shown by surface shading. Similarly, membranes 72, located on the outer sides of bridges 58 and 62. Each membrane 72 extends between a pair of longitudinally adjacent tabs 64 that extend from the outer sides of bridges 58 and 62. Membranes 70 and 72 are present to inhibit tissue growth between the features of the electrode array 40.

Electrode array 40 is also formed to have a head 74 and two shoulders 76. Head 74 is located forward center-located bridge 60. Each shoulder 76 extends forward from one of the two outer located bridges 58 or 62. Shoulders 76, while connected to head 70 by narrow beams, (beams not identified) are generally spaced apart from head 74. A more complete discussion of the geometry of the assembly head 74 and shoulders 76 is contained in the incorporated by reference U.S. Pat. App. No. 61/166,366.

An electrode 42 is disposed on each one of the tabs 64. The associated control module 44 is likewise seated, embedded in, the tab 64. Conductors 46 and 48 extend from each tab to the adjacent bridge 58, 60 or 62. If an electrode 42 does not function as a current source or sink, the electrode may function as a voltage probe. When an electrode 42 performs this function, the associated conductors 46 and 48 serve as the conductors over which the sensed voltage is connected to a monitoring circuit (not illustrated and not part of this invention).

By reference to FIG. 2 it can be seen that electrode array assembly 40 has a carrier 80 formed from a superelastic material; that is, a material that, after being subjected to the strain induced by appreciable rolling, folding or bending, returns to its initial shape. In one version of the invention, the carrier 80 is formed from a nickel titanium alloy such as Nitinol. Carrier 80 is shaped to form the basic geometric features of the assembly including base 56, bridges 58, 60 and 62, tabs 64, beams 66, head 74 and shoulders 76. Membranes 70 and 72 are formed from material different from which the carrier 80 is formed. In FIG. 2, electrode array assembly is shown active side up. The "active" side is the side of the array 40 on which electrodes 42 are exposed. Opposite the active side, electrode array 40 has a "passive" side, shown as the bottom side in FIG. 2.

Figure 26:
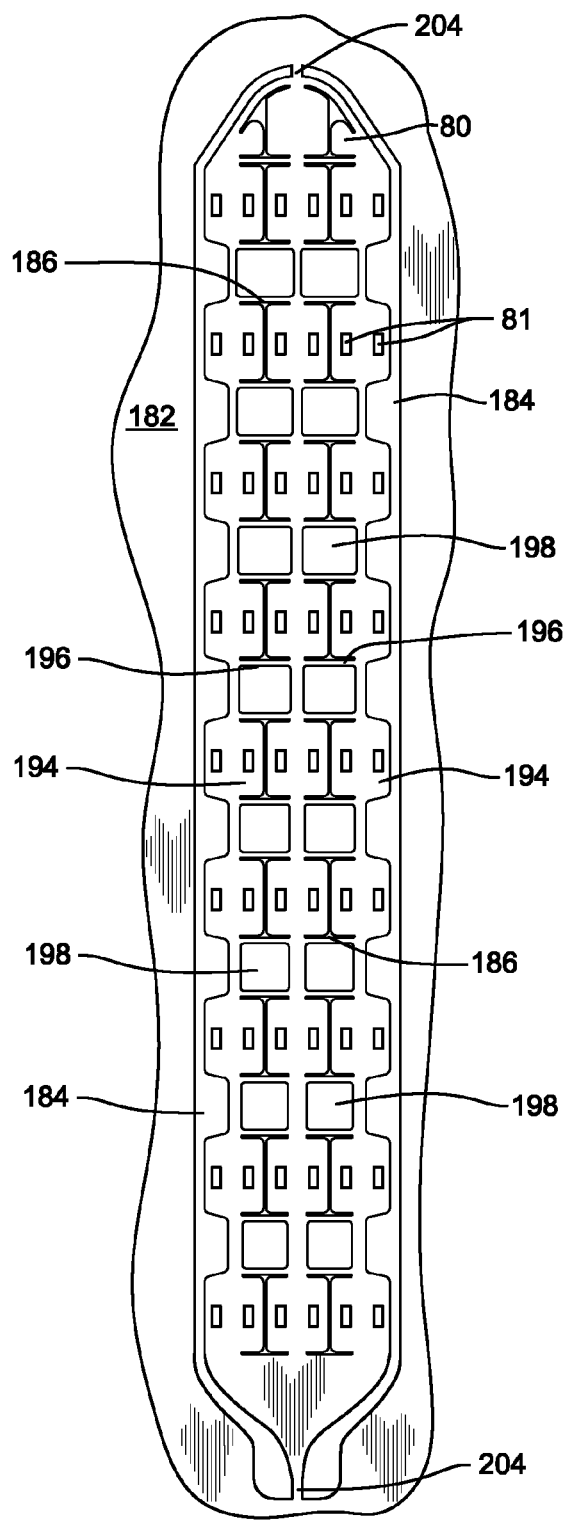
FIG. 26 is a plane view of a section of a coupon on which a carrier of this invention is formed.
Figure 26A:
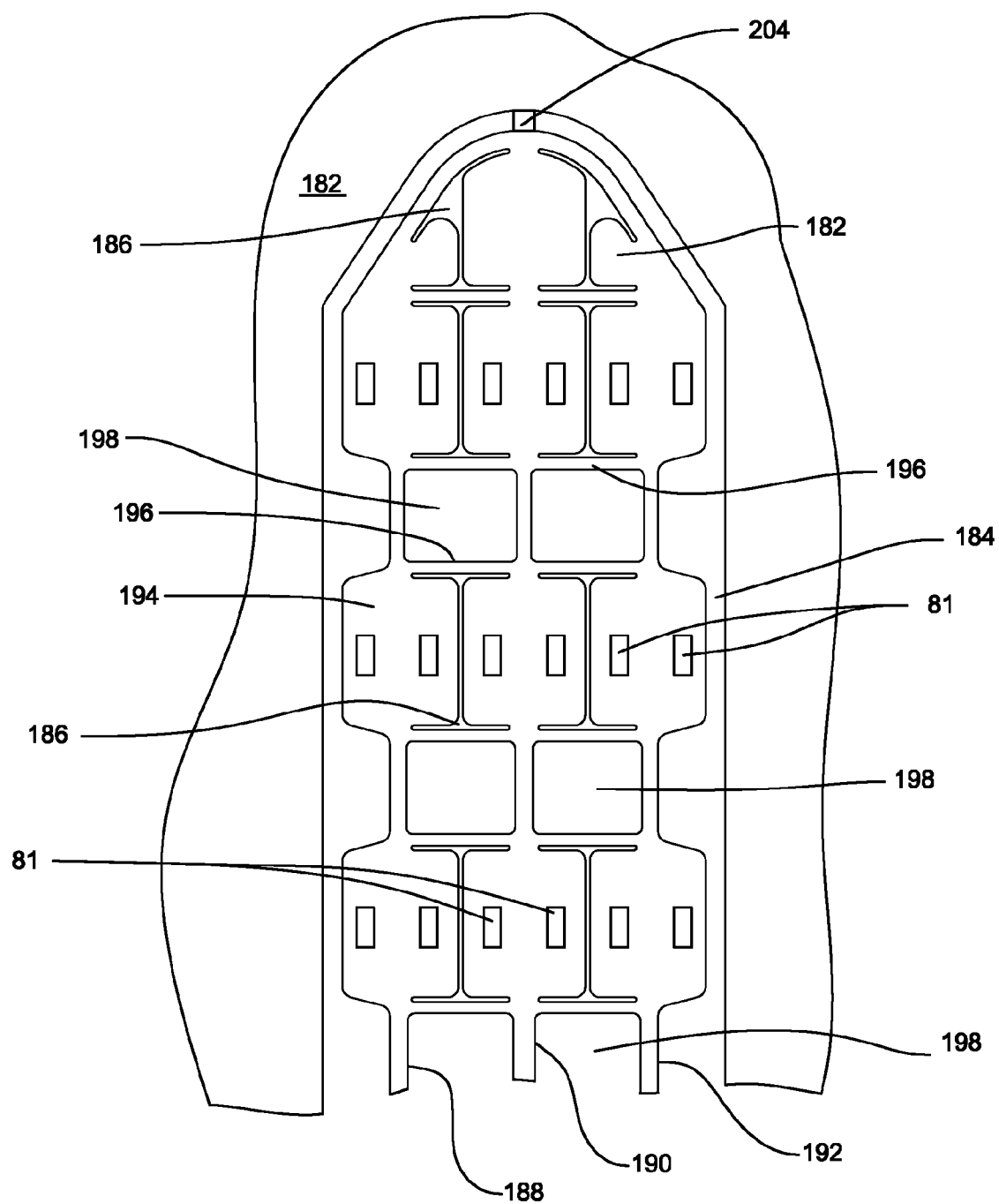
FIG. 26A is an enlarged plan view of the distal end of the carrier of FIG. 26.

Carrier 80 is formed with a number of windows 81, seen best in FIG. 26A. Each window 81 is formed in a separate one of the tab-defining sections of carrier 80. Returning to FIG. 2 it can be seen that frames 83 (one shown) formed from electrically insulating material, are located around the inner surfaces of carrier 80 that define the windows 81. A separate control module 44 is seated in each one of the windows 81 so as to be within the frames 83. The side surfaces of each control module 44 are encased in a shell 84 also formed from electrically insulating material. Shell 84 also has a panel that extends over the face of the control module 44 directed to the passive side of assembly 40. Thus, around the sides of the control module 44 both a section of the frame 83 and a section of the shell 84 separate the side surfaces of the control module from the adjacent surfaces of the carrier 80.

Figure 37:
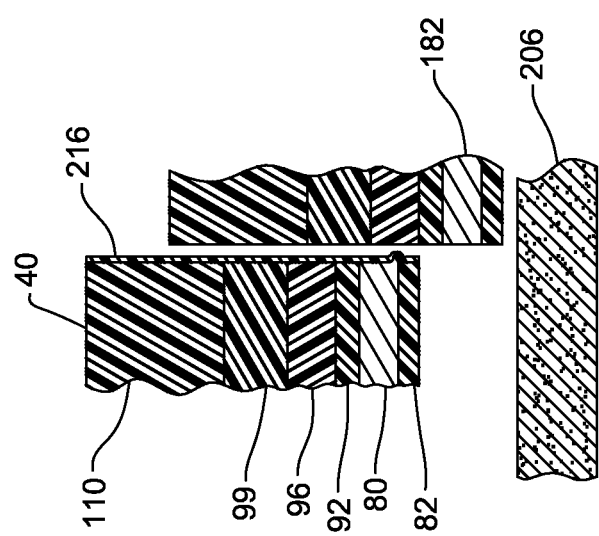
FIG. 37 depicts the lift off, the separation, of the electrode array from the substrate to which the array carrier was bonded.

Insulating material is disposed on the top, bottom and side surfaces of the carrier 80 (side-located insulating material only seen in FIGS. 36 and 37). One such electrically insulating material is a conformal coating such as the polyxylene polymer parylene-C. This insulating material is disposed over the surfaces of the carrier 80. The insulating material disposed over the surface of the passive side of carrier 80, the bottom side in FIG. 2, is identified as passive side insulating layer 82. In addition to covering the passive side face of frame 80, passive side insulating layer 82 extends over the side edges of the carrier 80.

Three different intermediate layers of insulating material, layers 92, 96 and 99 are disposed over the active side of carrier 80. Layers 92, 96 and 99 are formed from parylene. Intermediate insulating layer 92 is applied directly over the active side of carrier 80. Portions of layer 92 thus also cover the active side exposed face of control module 44 and the exposed rectangular carrier faces of the frames 83 and shells 84 that surround the modules 44. Conductors 46 are disposed over the intermediate insulating layer 92. A via 94 extends from a section of conductor 46 disposed over the control module through insulating layer 92 to a bond pad 91 (FIG. 7A) formed on the control module 44. Intermediate insulating layer 96 is disposed over insulating layer 92 and conductor 46. Conductors 48 are disposed over intermediate insulating layer 96. A via 98 extends from each bond pad 91 integral with each control module 44 to a section of the conductor 48 disposed over and associated with that control module 44. In FIG. 2, the individual layers of metal forming conductors 46 and 48 are shown. These layers are described and called out in the illustrated sequence of drawings that describe the assembly of electrode array 40 of this invention.

Intermediate insulating layer 99 is the outermost of the three intermediate insulating layers 99. Intermediate insulating layer 99 extends over intermediate insulating layer 96 and conductors 48.

Electrodes 42 are disposed over the intermediate insulating layer 99. Each electrode 42 includes a base pad 101 that is disposed on the outer surface of the intermediate insulating layer 99 so as to be at least partially disposed over the control module 44 and conductors 46 and 48. Each electrode base pad 101 includes a layer of titanium 102 that is in contact with the intermediate insulating layer 99. A layer of gold 103 is disposed over titanium layer 102. A layer of titanium 104 is disposed over the exposed surface of gold layer 103. A via 106, formed of gold, extends from gold layer 103 to a bond pad 91 integral with the associated underlying control module 44. Each via 106 thus extends through the intermediate insulating layers 92, 96 and 99. Spaced apart conductive buttons 107 are disposed over the outer surface of titanium layer 104. Each conductive button 107 includes a titanium layer 108 that is disposed on the base pad titanium layer 104. A thin layer of iridium or iridium oxide 109 is disposed over each titanium layer to complete the conductive button. The exposed faces of the iridium layers 109 of the conductive buttons are the conductive surfaces of each electrode that contact the tissue to which the electrode is applied.

An outer insulating layer, layer 110, is disposed over intermediate insulating layer 99. Outer insulating layer 110 is formed from the same material from which insulating layers 82, 92, 96 and 99 are formed. Outer insulating layer 110 is also disposed over portions of the electrodes 42. More particularly, portions of insulating layer 110 are disposed over the sections of the electrode titanium layer 104 located between the conductive buttons 107. Small sections of insulating layer 110 also surround the outer perimeters of the exposed iridium faces of the buttons 107. Openings 112 in outer insulating layer 110 function as access holes through which the tissue can pass across insulating layer 110 and contact the conductive buttons 107 integral with the electrodes 42.

Often electrode array 40 of this invention will have a thickness, the distance from the exposed face of passive side insulating layer 82 to the exposed face of outer insulating layer 110 of no more than 200 microns. In many cases this thickness is 150 microns or less and in still more preferred versions of the invention, this thickness is 100 microns or less. The side-to-side width across the array 40 is a function of the number of columns of electrodes 42. In the illustrated version of the invention, where there are 6 columns of electrodes 42, the width is typically 15 mm or less and often 10 mm or less. Similarly, the length of the array 40 is a function of the number of rows of electrodes 42. In the version of the invention illustrated in FIG. 1 wherein there are 9 rows of electrodes 42, the top-to-bottom length of the array is 100 mm or less and can be 70 mm or less. In FIG. 2 and the subsequent Figures, the layers of material forming the components of electrode array 40 are not shown to scale unless otherwise stated. This is to facilitate illustration of the components of this invention.

Figure 3:
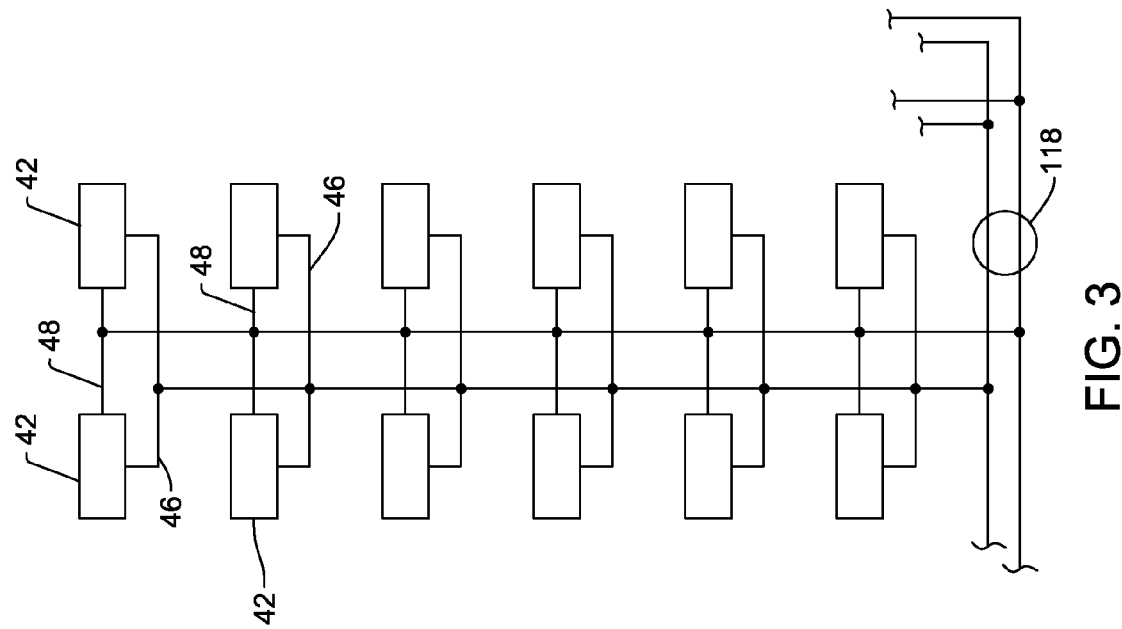
FIG. 3 is a block diagram of how signals are distributed to the individual control modules of the array over a bus.

As seen in FIG. 3, in at least some versions of the invention, each pair of conductors 46 and 48 forms a set of the lowest order branches from a two-wire bus 118. In FIG. 3, the two conductors forming bus 118 are shown as each having three first order branches, only one of which is completely illustrated. This reflects that each one of the first order branches extends over a separate one of the array bridges 58, 60 and 62. The control modules 42 associated with each bridge 58, 60 or 62 are tied to the branch of the bus that extends over the bridge. In FIG. 3 only six pairs of control modules are shown tied to the illustrated branch of bus 118. This is for ease of illustration only.

The exact structure of the control module 42 is not part of this invention and is not illustrated. For purposes of understanding the electrode array 40 of this invention, it should be understood that each control module 42 includes a node controller. One function of the node controller is to provide the physical connection between conductors 46 and 48, and therefore bus 118, and the other components internal to the module. A second function of the node controller is to, based on instructions received over the bus 118 and conductors 46 and 48, selectively actuate the other circuits internal to the control module 42. A power supply circuit harvests and stores the energy contained in the signals transmitted over the bus. The power supply circuit also stores the energy and uses the stored energy to power the other sub-circuits internal to the module 44. Control module 44 also contains a current source and a current sink, both of which are selectively tied to the electrode 42. Control module 44 also includes an analog to digital converter that is also tied to the electrode 42.

Figure 4:
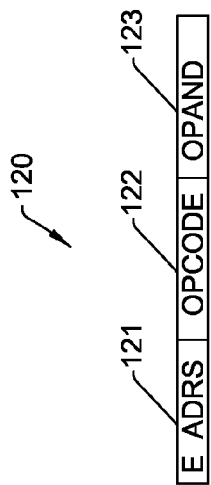
FIG. 4 depicts the components of a control packet distributed over the bus.

FIG. 4 represents the command packet 120 that may be transmitted over the bus 118 to the electrodes 42. One component of the packet 120 is an address field 121 (E ADRS). Address field 121 identifies the individual control module 44 for which the command contained in the packet 120 is intended. An opcode (OPCODE) field 122, also a component of the command packet 120. The opcode field 122 is the specific instruction that is to be taken by the control module 44. Examples of such instructions include: activate current source; activate current sink; and active analog to digital converter so a reading of the voltage present at the electrode may be obtained. Some command packets 120 also include an operand (OPAND) field 123. The operand field 123 contains data indicating the value associated with the operand. An example of a value contained with an operand is the level of the current draw to which the current sink should be set when activated.

The protocol by which signals are transmitted over bus 118 to and from the control modules 44 is not part of the present invention.

In FIGS. 1 and 1A the conductors forming bus 118 appear as lines extending over the array base 56 and bridges 58, 60 and 62. This is for purposes of illustration only. In actually, the bus conductors, like conductors 46 and 48, are covered by insulating layers and are not visible. Also, not illustrated in the Figures are the connection between the on-carrier conductors forming bus 118 and the individual conductors internal to cable 50. This bonding may be achieved by micro-ball bonding.

An electrode array 40 of this invention can be constructed to have 10 or more and even 20 or more electrodes 42 each of which can be individually controlled. An advantage of the array 40 having this number of electrodes is that it allows the practitioner to precisely target through which tissue the current is flowed. This allows the practitioner, often through experimentation, target the current flow through the patient so that the current flow offers an appropriate balance between beneficial effects and tolerable side effects. Even when having this relatively large number of electrodes, the power and commands supplied to the electrodes be supplied over an implanted cable 50 with just two conductors. This minimization of the number of conductors in cable 50 makes it possible to implant the conductors using minimally invasive surgical techniques.

Furthermore, it is anticipated that in many versions of the invention, each control module 44 will function as the current source and sink to no more than eight individual electrodes 42 and more preferably no more than four individual electrodes 42. In the above described version of the invention, each electrode 42 has its own dedicated control module 44. Accordingly, the power source/sink signals generated by each control module typically has to travel a distance of no more than 10 cm usually, often 3 cm or less and more preferably 0.5 cm or less. An advantage of this construction of the invention is that the power required to precisely source/sink currents over these relatively small distances is less the power required to source/sink currents from a device external to the array. Consequently, a portable power source built into the IDC 52 can provide power for a longer time than if the source was required to provide power to individual electrodes spaced 15 cm or more from the IDC 52.

The thin passive side-to-active side profile of array 40 and that the carrier 80 is formed from material that if, not superelastic is at least flexible both facilitate the implantation of the array using minimally invasive medical techniques. For example, prior to implantation the array could be rolled or folded into a cannula having a lumen with a diameter less than the unrolled/unfolded width of the array. The cannula is directed to the target location in the body at which the array is to be deployed. The array is inserted into the body through the cannula. Once the array is discharged from the cannula, the array is unrolled/unfolded over the tissue through which the current is to be flowed.

The parylene forming the layers 92, 96 and 99 through which the vias 94, 98 and 106 extend are flexible. This reduces the mechanical stress to which the vias themselves are exposed. Each via 94, 98 and 106 has a maximum diameter of 80 microns and typically 50 microns in diameter or less. This means that the vias themselves are not so large in cross sectional size that they are not able to themselves flex. The vias themselves are connected directly to the bond pads 91 integral with the control module 44. The need to provide very thin, and therefore very fragile, wire bonds to the control module is eliminated. Further the maximum height of the vias, is typically 100 microns or less and often 50 microns or less. In the version of the array illustrated in FIG. 2, vias 106 are the tallest vias. As a consequence of the vias 95, 98 and 106 being of relatively short height, they are not exposed to large mechanical stresses. Likewise, conductors 46 and 48 and the conductors forming bus 118 have heights that are typically less than 5 microns and often 3 microns or less. The widths across these conductors are usually 75 microns or less and may be 40 microns or less. These design features facilitate the flexibility of these conductors. Collectively, these design features of the electrode array 40 of this invention reduce the likelihood that the mechanical vibrations and shocks to which the array is invariably subjected will so stress these electrical connections that the connections break.

While both the parylene layers 92, 96 and 99 the underlying assembly substrate, carrier 80, are flexible, the carrier is less flexible than the parylene layers. The reduced flexibility, increased rigidity, of the carrier is what causes the electrode array assembly 40 to conform to the surface of the tissue against which the assembly is deployed. This feature of the assembly 40 is what holds the assembly electrodes 42 against the tissue to which the therapeutic current is to be applied.

Likewise, even though the array 40 may have 20 or more electrodes 42 it can be possible to provide cable 50 with often four or less and often just two individual conductors over which current is sourced to and instructions are provided to all of the electrodes. This means these conductors, which are not attached to a substrate, may themselves be relatively thick, for example 50 micron or more in diameter and sometimes 100 microns or more in diameter. This facilitates the formation of conductor-to-array bonds with these conductors that are less fragile than the bonds used to hold thinner conductors to the array. This reduction in bond fragility means that it is less likely that, over time, owing to the inevitable mechanical shock to which the array is exposed, one of the bonds will break.

II. First Method of Assembly

Figure 5:
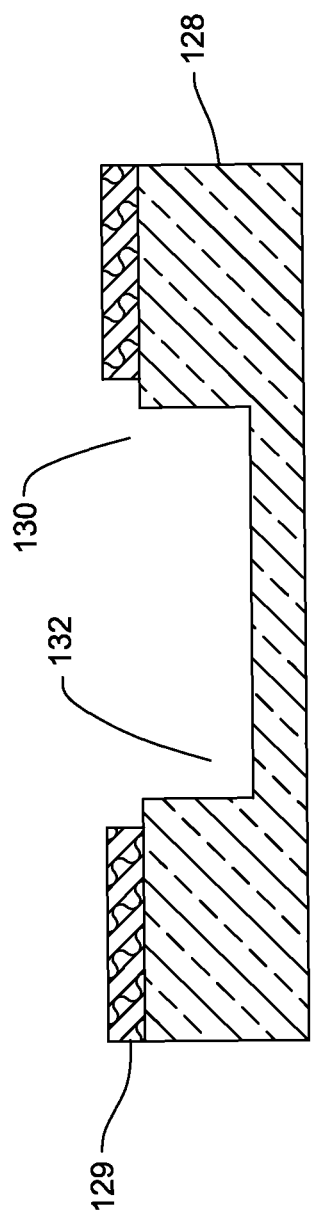

One method of assembling electrode array 40 of this invention is now explained by initial reference to FIG. 5. Initially, a layer of photo resist 129 is disposed over a substrate, here a silicon wafer 128. (Step not illustrated.) Openings 130 (one shown) are formed in the photo resist 129 at the locations where the control modules 44 are to be seated in the silicon wafer 128. Once openings 130 are formed in the photo resist layer 129, using a reactive ion etching process, openings 132 (one shown) are formed in the silicon wafer 128. The openings 132 is formed so that the portions of the wafer 128 that define the openings are located inwardly of the portions of the photo resist 129 that define the perimeter of photo resist openings 132.

As represented by FIG. 6, with photo resist layer 129 still in place, boron is diffused into exposed sections of the silicon wafer 128 that are located inwardly of photo resist openings 130. The boron are diffused approximately 25 microns into the silicon wafer 128. This boron thus diffuses into the portions of the silicon wafer that define the side walls around the bases of wafer openings 132. The boron diffused sections of silicon become the shells 84 (one shown) of assembly 40 and are therefore identified out as such in the Figures. Photo resist layer 129 is then removed from the silicon wafer 128, (step not shown).

Figure 7A:
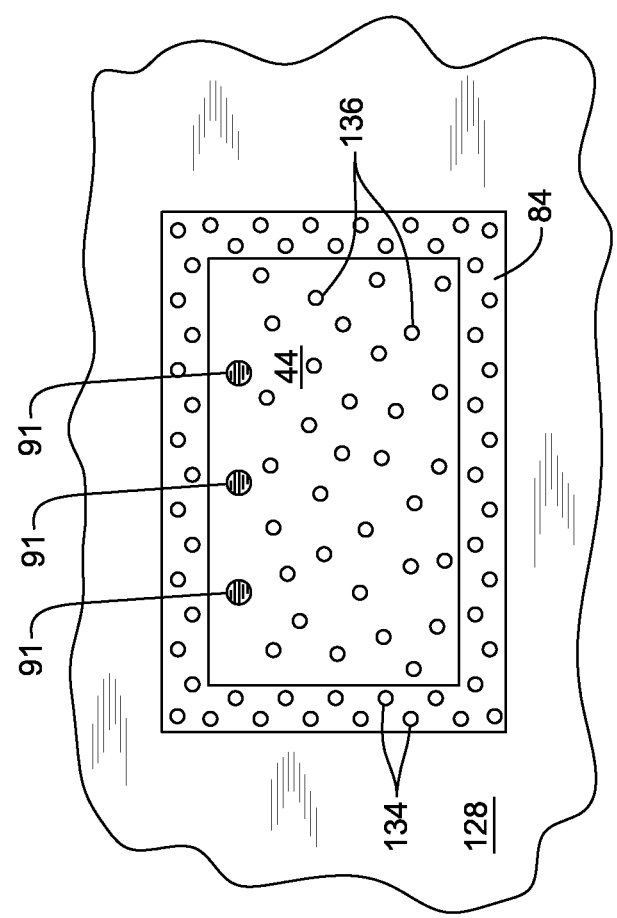
FIG. 7A is a top plan view of control module seated in the shell.

As a consequence of the formation of shells 84, each shell 84 has an exposed face 85, seen in FIG. 7, that is generally in the shape of a rectangular frame. Using a reactive ion etching process, small bores 134 are formed in the exposed faces of the shells 84. Bores 134 have a diameter of approximately 0.2 to 1 micron and extend no greater than 10 microns deep into the shell 84. To minimize the complexity of the later Figures, bores 134 are only illustrated in FIGS. 7 and 7A. It should be appreciated that, in this etching process, as well as in a number of processes in the assembly of electrode array 40, include the sub-steps of applying a photo resist layer, selectively removing portions of the photo resist layer and removing the photo resist layer. Many of these individual sub-steps, as they apply to the formation of bores 134 and other below described processes are neither described nor illustrated.

A control module 44 is then seated in each silicon wafer opening 130 as represented by FIG. 8. The control module 44 is disposed in the shell 44 so that the face of the module on which the bond pads 91 are formed faces outwardly. Control module 44 has a top-to-bottom height that is typically 2 microns or less then the depth of the wafer opening. Accordingly, as represented by FIG. 9, the next step in the assembly of the electrode-control module-conductor sub-assembly is the removal of the upper sections of the silicon wafer 128 and shells 84 that extend above control modules 44. This removal process is performed by mechanical lapping, removing the outer layers of both the wafer and the shells. As part of the lapping process, the exposed the die, shell and wafer are cleaned. This cleaning step is the only inter-step cleaning step described. Neither this cleaning step nor any of the other cleaning steps are illustrated. This cleaning is performed in part to remove debris from shell bores 134. Uniformity of the levels of the die, the wafer and shell are then checked, step not illustrated.

Small closed end bore holes 136, seen in FIG. 7A, are then formed in the exposed face of the die forming control module 44. Bores 136 have a diameter of between 1 and 2 microns and a depth of no more than 10 microns. Holes 136 are formed by a reactive ion etching process. To minimize the complexity of the drawings, bores 136 are only illustrated in FIG. 7A.

A first insulating layer, intermediate insulating layer 92, is then applied over the coplanar surfaces of the control modules 44, shells 84 and silicon wafer 128, as represented by FIG. 10. Intermediate insulating layer 92 has a thickness of no greater than 20 microns. Parylene is a conformal coating. During the vapor deposition process in which the parylene of intermediate insulating layer 92 is applied, a fraction of the parylene flows into the shell bore 134 and die bores 136. The parylene in bores 134 and 136 holds the parylene forming insulating layer 92 to the surfaces of the dies 44, shells 84 and wafer 128.

During the process of forming intermediate insulating layer 92, the parylene is applied to cover a surface area larger than that subtended by the individual electrodes. The parylene is applied to cover a surface area that typically is greater than the surface area of the electrode array 40. In the subsequent described steps in which insulating layers 82, 96, 99 and 110 are formed, the parylene is similarly applied to cover the same surface area as the parylene forming insulating layer 92. The reason for this relatively wide surface application of the parylene is discussed below.

FIG. 11 illustrates that holes 138 (one shown) are formed in intermediate insulating layer 92. Each hole 138 is in registration over the control module bond pad 91 to which the associated conductor 46 is connected. Holes 138 are formed by, first, applying a photo resist layer over insulating layer 92. Openings are formed in the photo resist layer where the holes 138 are located. An oxygen plasma etching process is used to form the holes 138. Holes 138 have a diameter equal to that of the vias 94 (FIG. 2) that will subsequently be formed in the holes. The photo resist layer is then removed.

Figure 12:
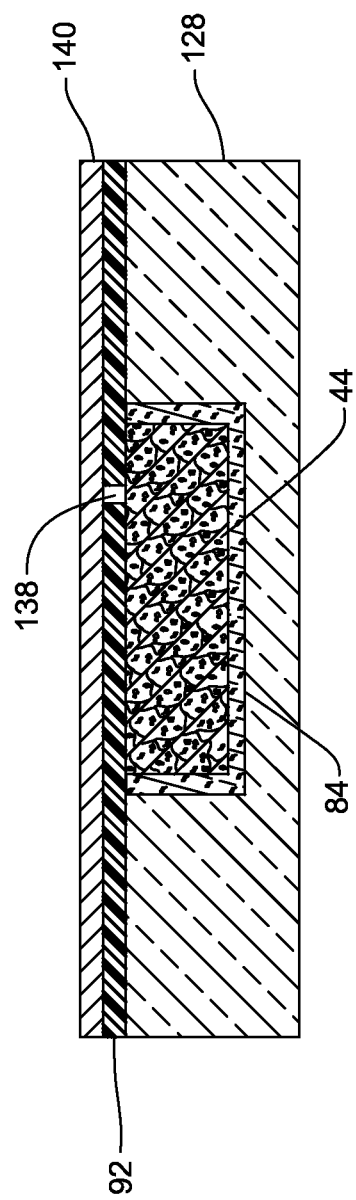

Once holes 138 are formed, a layer of titanium 140 is vapor deposited over intermediate insulating layer 92 as represented by FIG. 12. Titanium layer 140 has a thickness of no greater than 5000 Angstroms. The titanium of layer 140 functions as an adhesion layer for the next applied layer 142. Gold is then vapor deposited over titanium layer 140 as seen by FIG. 12 so as to form layer 142. The gold of layer 142 has a thickness of no greater than 5000 Angstroms. The gold of layer 142 functions as a seed layer for the next layer of gold that is of substantially greater thickness.

Figure 13:
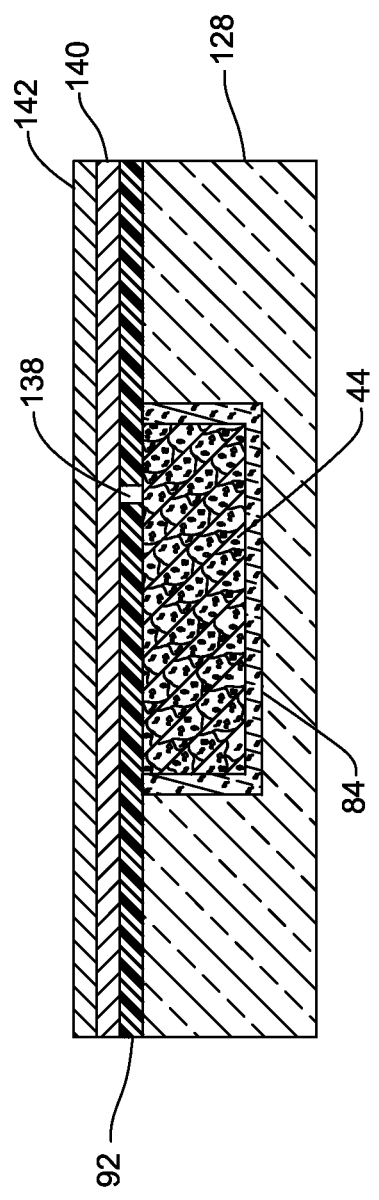
Figure 20:
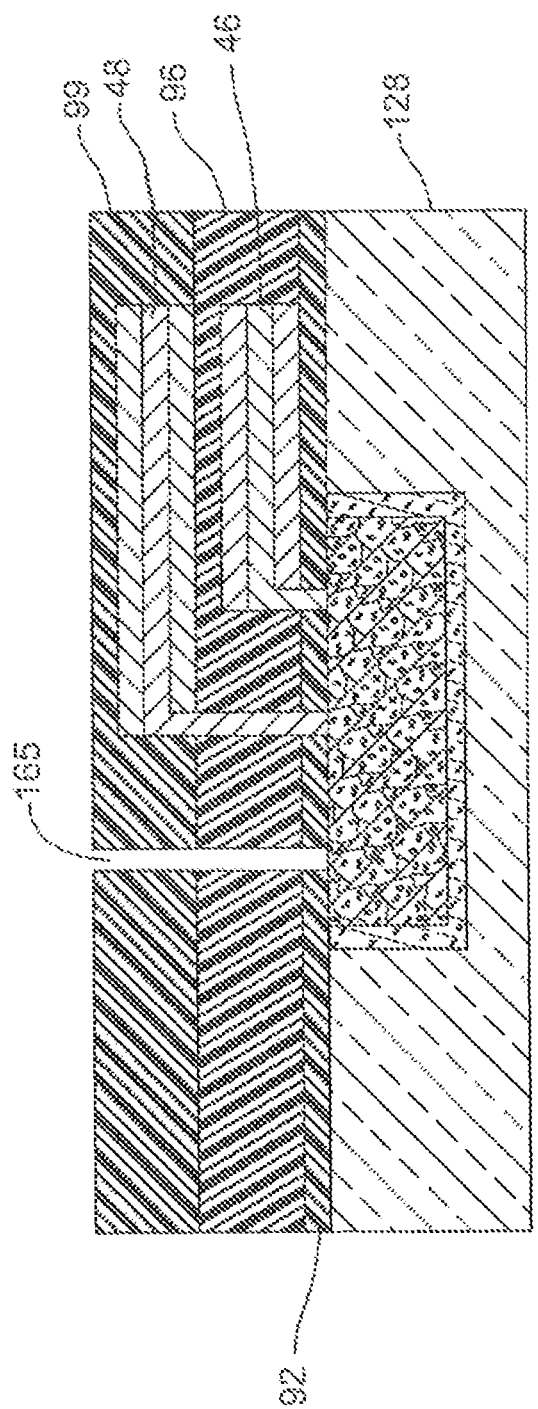

In FIGS. 12 and 13, the titanium of layer 140 and the gold of layer 142 are shown as extending over the hole 138. This is for ease of illustration. In actuality very small amounts of the titanium and gold that, respectively, form layers 140 and 142 flow into the hole 138. The same is true for the titanium adhesion layers and gold seed layers disposed over holes 154 (FIG. 17) and holes 165 (FIG. 20).

Figure 14:
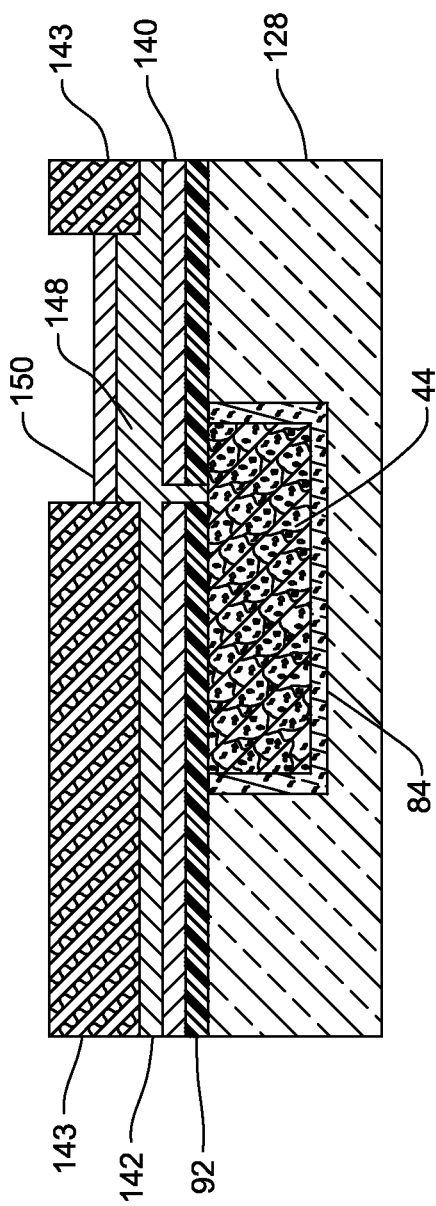

It should be understood that titanium layer 140 and gold layer 142 are deposited over substantially the whole of intermediate insulating layer 92. Fabrication of conductors 46 and the associated conductor of bus 118 continues with the application of a photo resist layer 143 over gold layer 142. Openings are formed in the photo resist layer 143 to expose the sections of the gold layer 142 over which the conductors 46 are to be formed. Gold is applied by an electroplating process over the exposed surfaces of gold layer 142. In FIG. 14 and the subsequent Figures the gold applied over the assembly from these two process form a single layer, called out to the right of the control module 44 in FIG. 14 as layer 148. Layer 148 has a thickness of approximately 2 microns.

As a consequence of the application of the gold forming layer 148 a portion of the gold flows into the openings 138 formed in insulating layer 92. This gold bonds with the underlying control module contact pads 91 so as to form the vias 94 that extend to conductors 46.

Titanium adhesion layer, layer 150 in the Figures, is then applied by a vapor deposition process over the exposed surface of gold layer 148. Titanium adhesion layer 150 typically has a thickness no greater than 5000 Angstroms. While not illustrated, some of the titanium deposited in this process covers the exposed surface of photo resist layer 143. extend over Photo resist layer 143 is then removed, step not shown. As shown in FIG. 14, photo resist layer 143 extends above titanium adhesion layer 150. Consequently, the photo resist layer 143 can be removed by a chemical lift off process. As a consequence of this process, the titanium deposited on top of the photo resist layer 143 is also transported away from the electrode-control module-conductor assembly. The removal of photo resist layer 143 exposes the portions of the titanium layer 140 and gold seed layer 142 that do not form part of the conductors 46.

Figure 15:
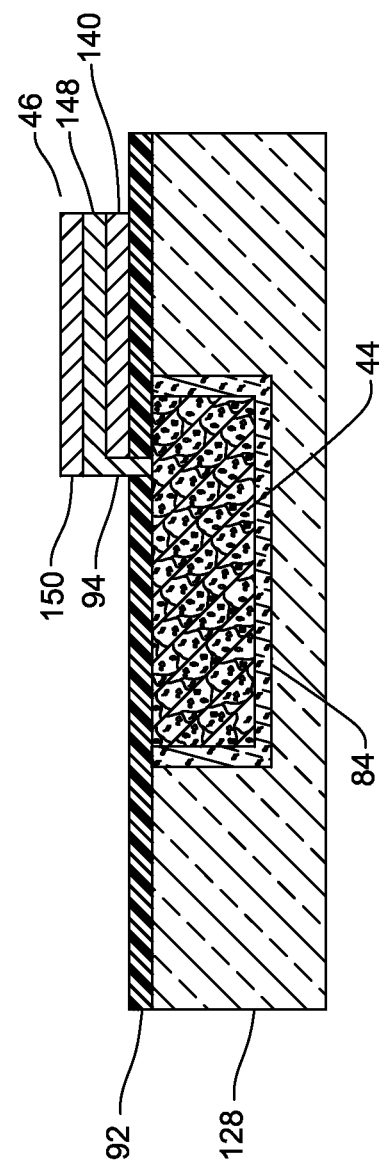

Masks are then deposited over the conductor 46 and the conductor of bus 118, step not shown. A gold-specific chemical etch process is employed to remove the exposed gold seed layer 142. A titanium-specific chemical etch process is then employed to remove the sections of the titanium layer 140 previously covered by the gold seed layer 142. The masks are then removed. As a consequence of the removal of layer 140 and 142, as seen in FIG. 15, what is left on the intermediate insulating layer 92 are sections of laminate that comprise a titanium layer 140 a gold layer 148 and a titanium layer 150. These laminate structures are the conductors 46. Other ones of the laminate structures form the conductors of bus 118.

In FIG. 15 and the subsequent Figures the gold layer 148 of conductor 46 as well as the gold layer 162 of conductor 48 (FIG. 18) and the gold layer 103 of the electrode 42 (FIG. 23) are shown as being of the same thickness as the adjacent titanium layers. This is for ease of illustration only. As indicated by the above stated dimensions, these gold layers are typically at least 4 time larger in thickness than the adjacent titanium layers.

Figure 16:
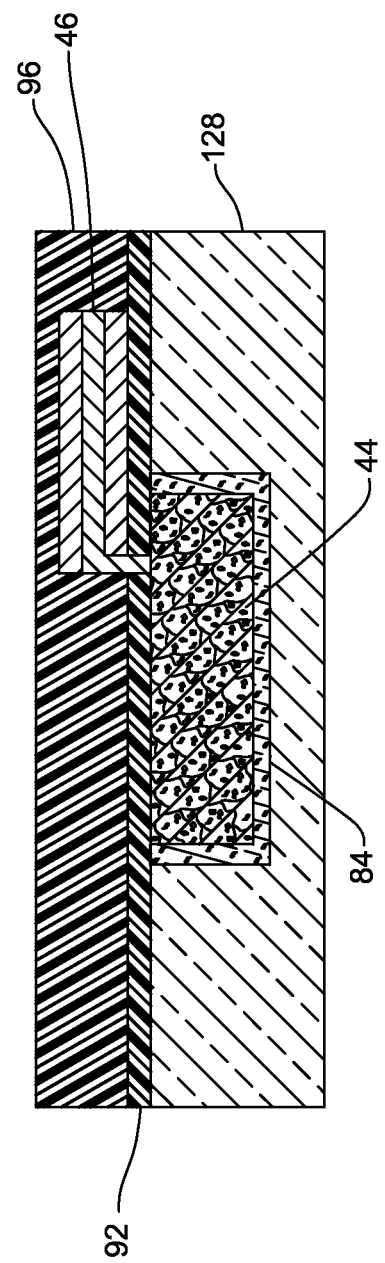
Figure 17:
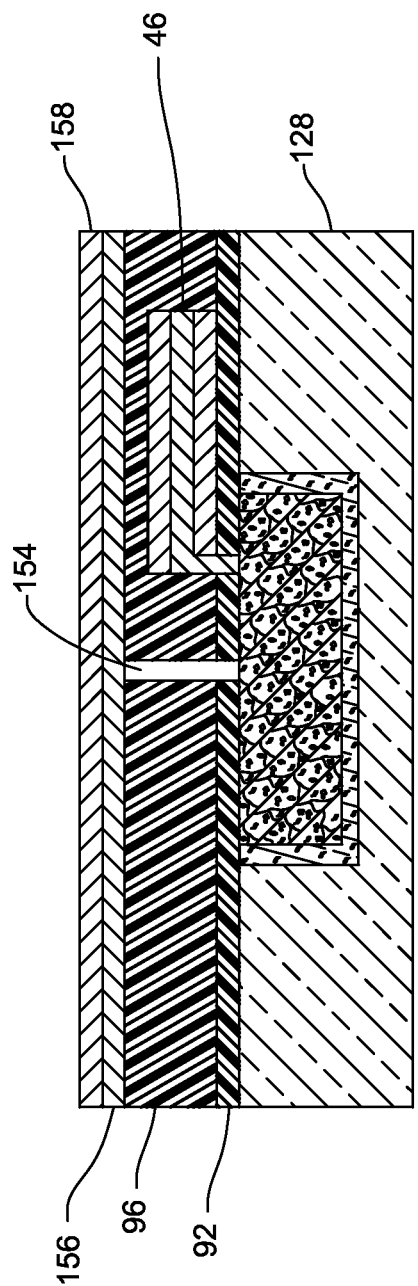

Once conductors 46 and the associated bus conductor are formed, parylene is applied over the conductor 46 as well as intermediate insulating layer 92 to, as illustrated by FIG. 16, forming intermediate insulating layer 96. In regions where the parylene forming insulating layer 96 is applied directly over insulating layer 92, layer 96 has a thickness is typically 10 microns or less. In FIGS. 2 and 16 and in the following Figures, the portion of insulating layer 96 disposed over conductor 46 appears to have a lesser thickness than the portion of layer 96 disposed directly onto layer 92. This is for ease of illustration only. In actuality, the thickness of insulating layer 96 is generally uniform over the different components of the assembly on which the parylene forming the layer is applied. In some versions of the invention layer 96 has a thickness of approximately 10 microns. As seen in FIG. 17, holes 154 (one shown) are formed in intermediate insulating layer 96. Each hole 154 is centered over the die bond pad 91 to which a via 98 extends. Each hole 154 thus extends through both the intermediate insulating layer 96 and the underlying intermediate insulating layer 92. Each hole 154 has the diameter of the via 98 (FIG. 2) that will be subsequently formed in the hole 154.

Figure 18:
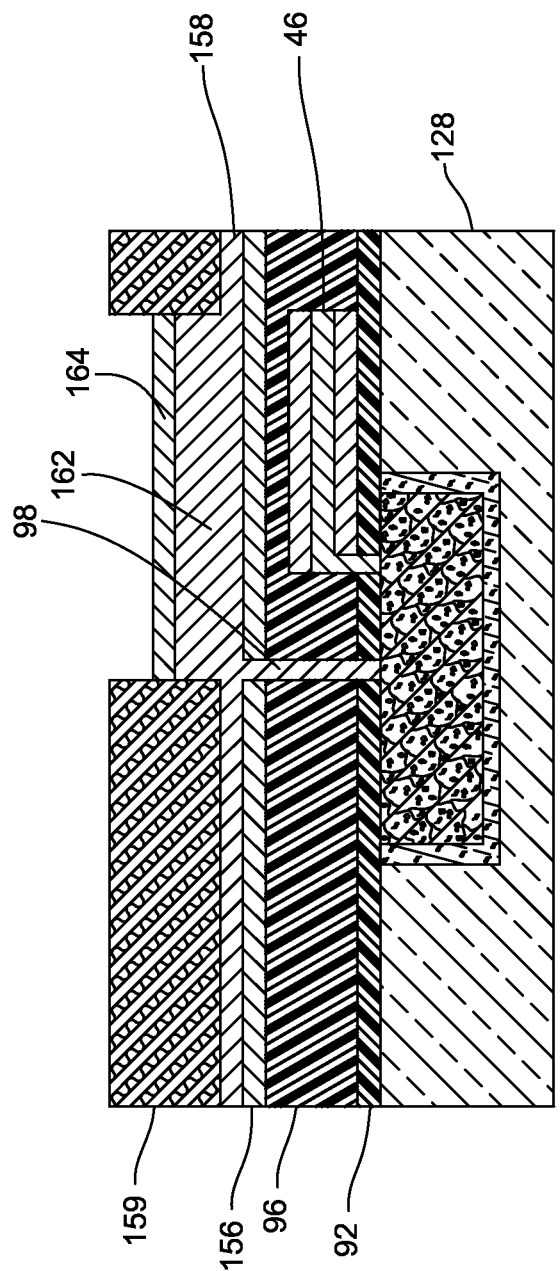
Figure 19:
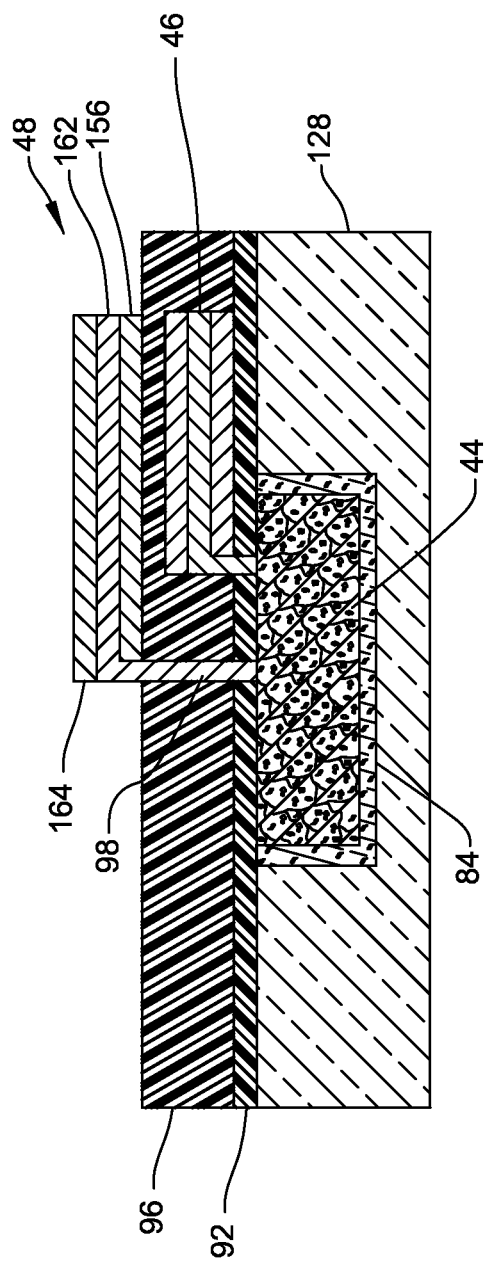

FIGS. 17, 18 and 19 represent that conductors 48 are formed in the same general manner in which conductors 46 are formed. Layers of titanium and gold, respectively layers 156 and 158, are disposed over intermediate insulating layer 96. Not illustrated are small amounts of titanium and gold that form layers 156 and 158 that flow into holes 154. A mask 159 is applied over the surfaces of gold layer 158 that are not to be part of the conductors 48 and associated bus 118 conductor. Gold is electroplated over the sections of gold layer 158 that are open through the mask 159. In FIG. 18 the relatively thick layer of gold formed by this layer and the underlying gold layer 158 is called out as layer 162. A titanium layer 164 is applied on top of gold layer 162. Titanium and gold layers 156, 162 and 164 have the same thicknesses as, respectively, layers 140, 148 and 150.

As a consequence of this electroplating process, gold flows into holes 154 that extend through insulating layers 92 and 96. This gold bonds to the underlying control module contact pad 91 and forms via 96.

Mask 159 is then removed. The sections of first gold layer 158 and then titanium layer 156 previously covered by mask 159 are then removed. These removal processes are the same employed with respect to the removal of layer 140 and 142. As a result of the removal of these sections of layers 156 and 158. The electrode-control module-conductor assembly is left with the conductors 48 and associated bus 118 conductor. In FIG. 19 a single conductor 48, consisting of a laminate of layers 156, 162 and 164 is shown. Again, in FIG. 19 and the other Figures, the relative thickness of these layers is not shown.

The sub-assembly is then prepared for the fabrication of the electrodes 42. As depicted in FIG. 20, this process begins with the application of parylene to establish the outermost intermediate insulating layer, layer 99. Intermediate insulating layer 99 is thus disposed over the conductors 48, the associated bus conductor and the exposed surfaces of intermediate insulating layer 96. Where insulating layer 99 is disposed over insulating layer 96, layer 99 typically has thickness of 10 microns or less. While not apparent in the Figures, insulating layer, the thickness of insulating layer 99 is generally constant regardless of the assembly component over which the parylene forming the layer is applied. Once intermediate insulating layer 99 is formed, holes 165 (one shown) are formed in this layer, as well as underlying insulating layers 96 and 92. Each hole 165 is centered over the die bond pad 91 to which the associated electrode 42 is connected. Each hole 165 has the diameter of the via 106 that is to be subsequently formed in the hole.

Figure 21:
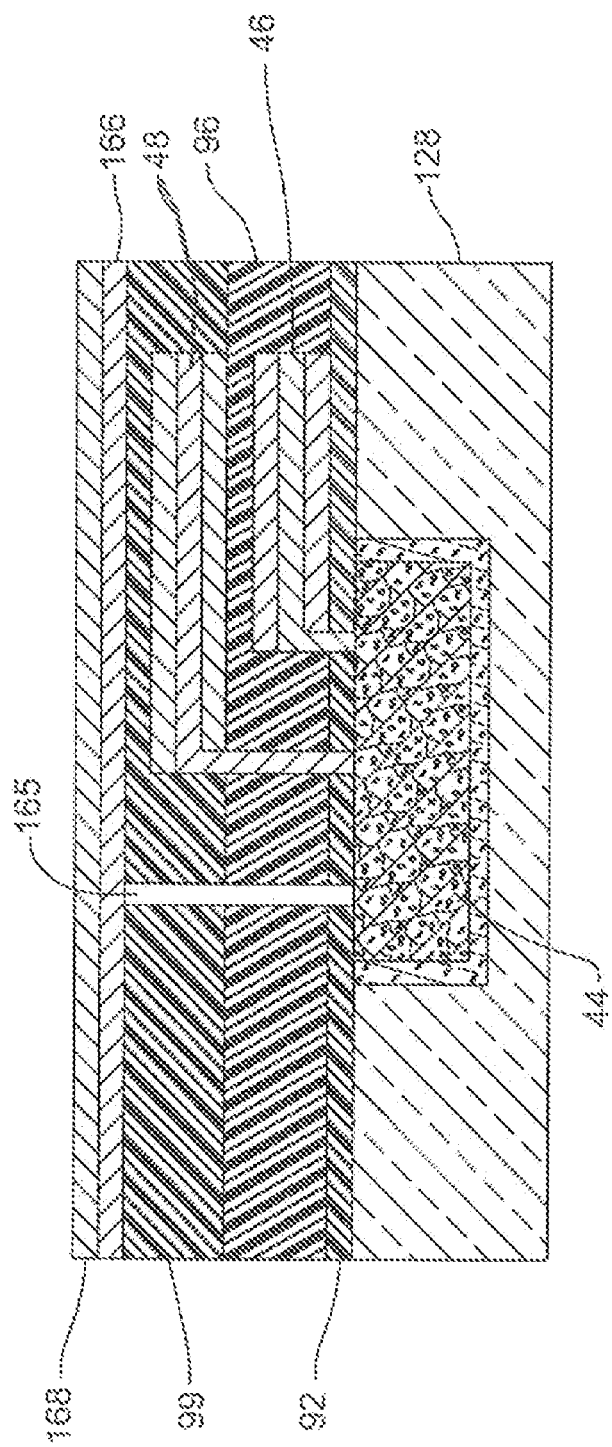

Once intermediate insulating layer 99 is applied to the sub-assembly, titanium and gold seed layers are applied to the assembly by separate vapor deposition processes to facilitate the fabrication of the electrode base pad. FIG. 21 illustrates that these layers, a titanium layer 166 and a gold layer 168 are applied over the whole of insulating layer 99. While not illustrated, a small fraction of the titanium and gold vapor released in this process flows into the holes 165.

Figure 22:
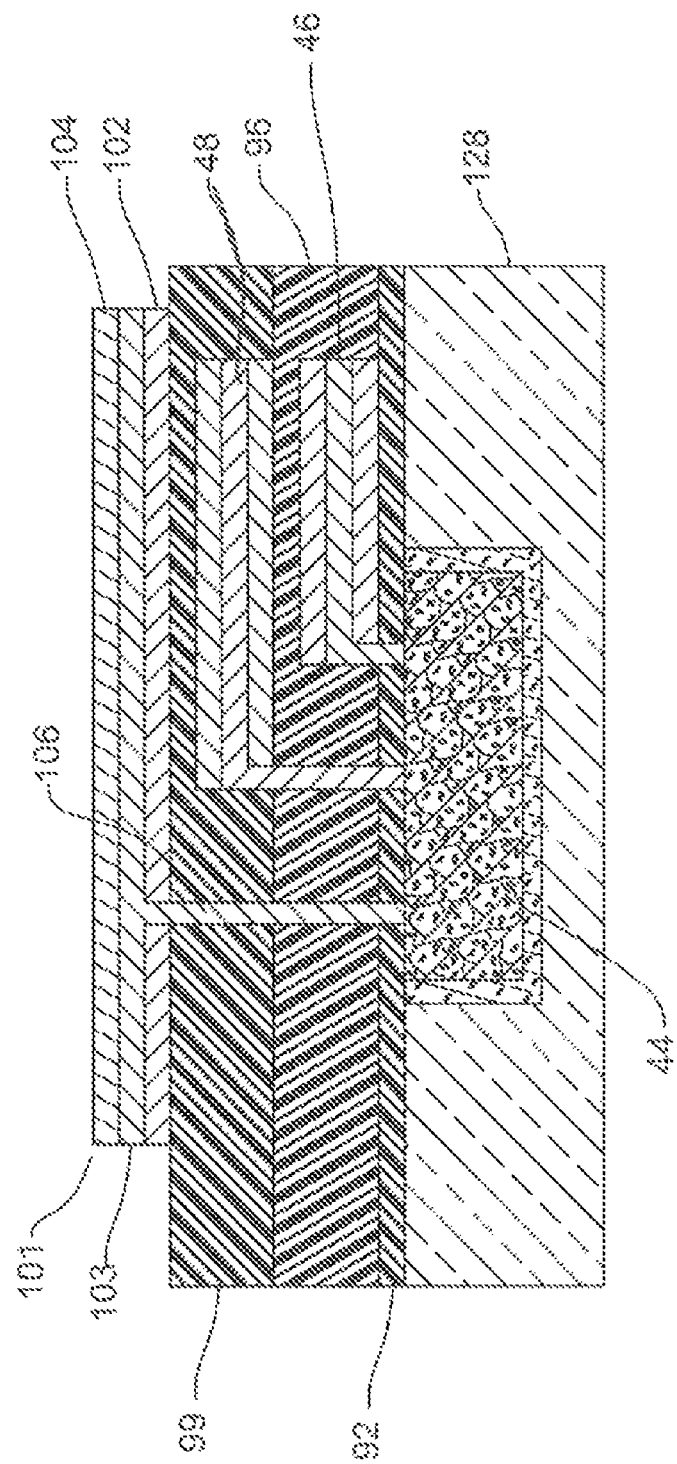

Once titanium layer 166 and gold layer 168 are applied, process steps are performed to increase the thickness of the gold layer and form a titanium adhesion layer adhesion layer on top of the gold layer. These process steps are the same as the process steps used to complete the formation of the conductors 46 and 48 and the conductors integral with bus 118. Accordingly, these steps are neither described nor illustrated. At the conclusion of this process, as seen in FIG. 22, the base pads 101 (one shown) of the electrodes 42 are formed as illustrated in FIG. 22. Titanium layer 102 has a thickness of typically less than 5000 Angstroms. Gold layer 103 has a thickness of approximately 20 microns. Titanium layer 104 has a thickness of typically less than 5000 Angstroms. Gold layer 103 is thicker than gold layers 148 and 164 is to increase the radio-opacity of the electrode array assembly 40 in the vicinity of the electrodes 42.

As part of the electroplating process in which the gold that forms the largest portion of layer 103 is applied, some of the gold flows into holes 165. This gold bonds to the underlying control module contact pad 91 so as to form the control module-to-electrode via 106.

Figure 23:
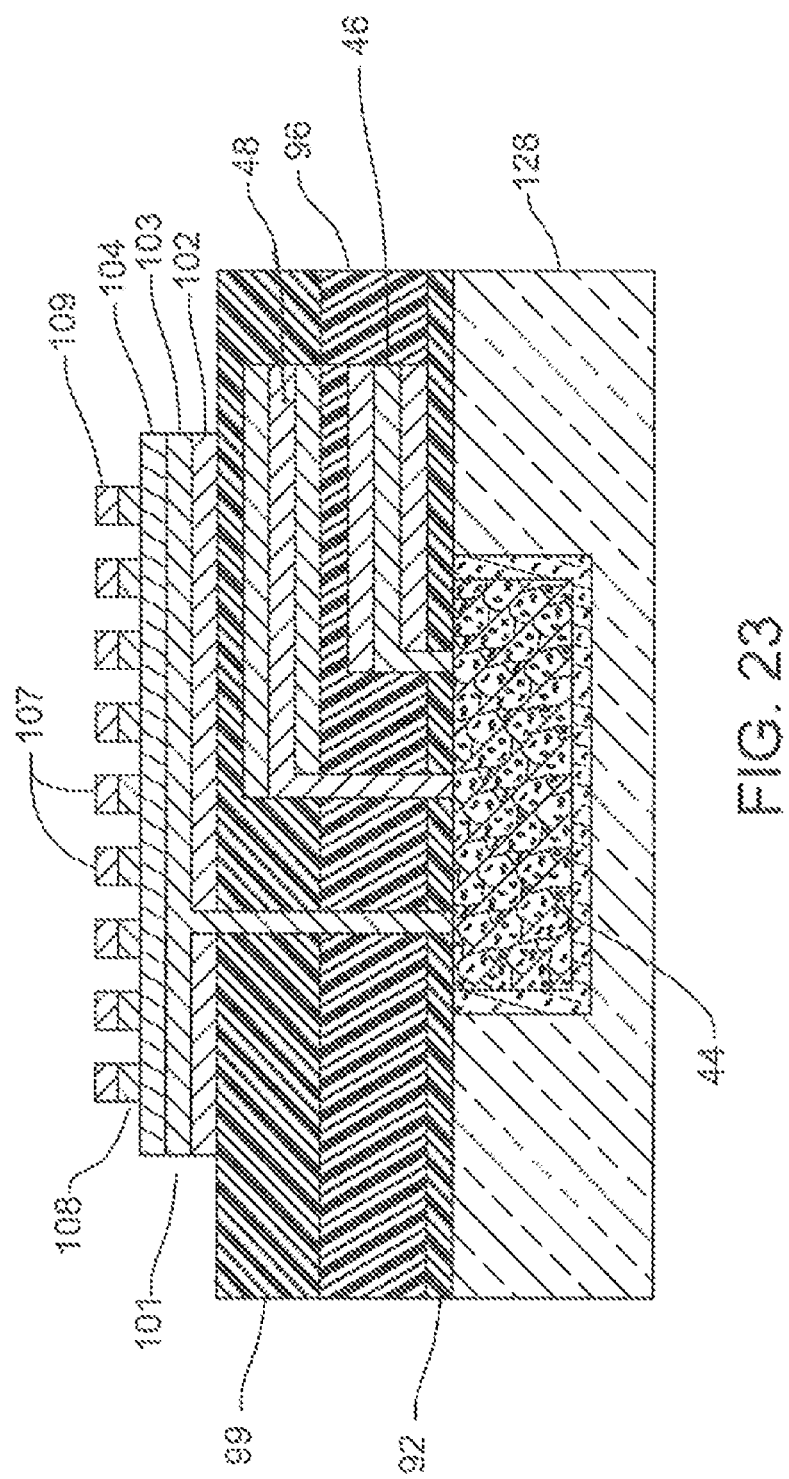

Conductive buttons 107 are then formed over the electrode base pads as seen by reference to FIG. 23. This process begins by the formation of a mask over the exposed titanium layer 104 (step not shown). This mask is formed so as to define openings in the sections of the electrode base pad titanium layers 104 over which the buttons 107 are to be formed. Once the mask is formed, titanium is sputtered over the assembly to form the individual titanium layers 108. Each titanium layer 108 typically has a thickness of less than 5000 Angstroms. Iridium or iridium oxide is then sputtered over the assembly to form button layers 109. Iridium layers 109 often have a thickness of less 30,000 Angstroms and more often less than 10,000 Angstroms. The buttons 107 formed in this process are typically rectangular cross sectional profile. Often the longest length along one of the side edges of a button is 125 microns or less. In some versions of the invention, the longest length along one of these edges is 60 microns or less. The photo resist mask is then removed.

Figure 24:
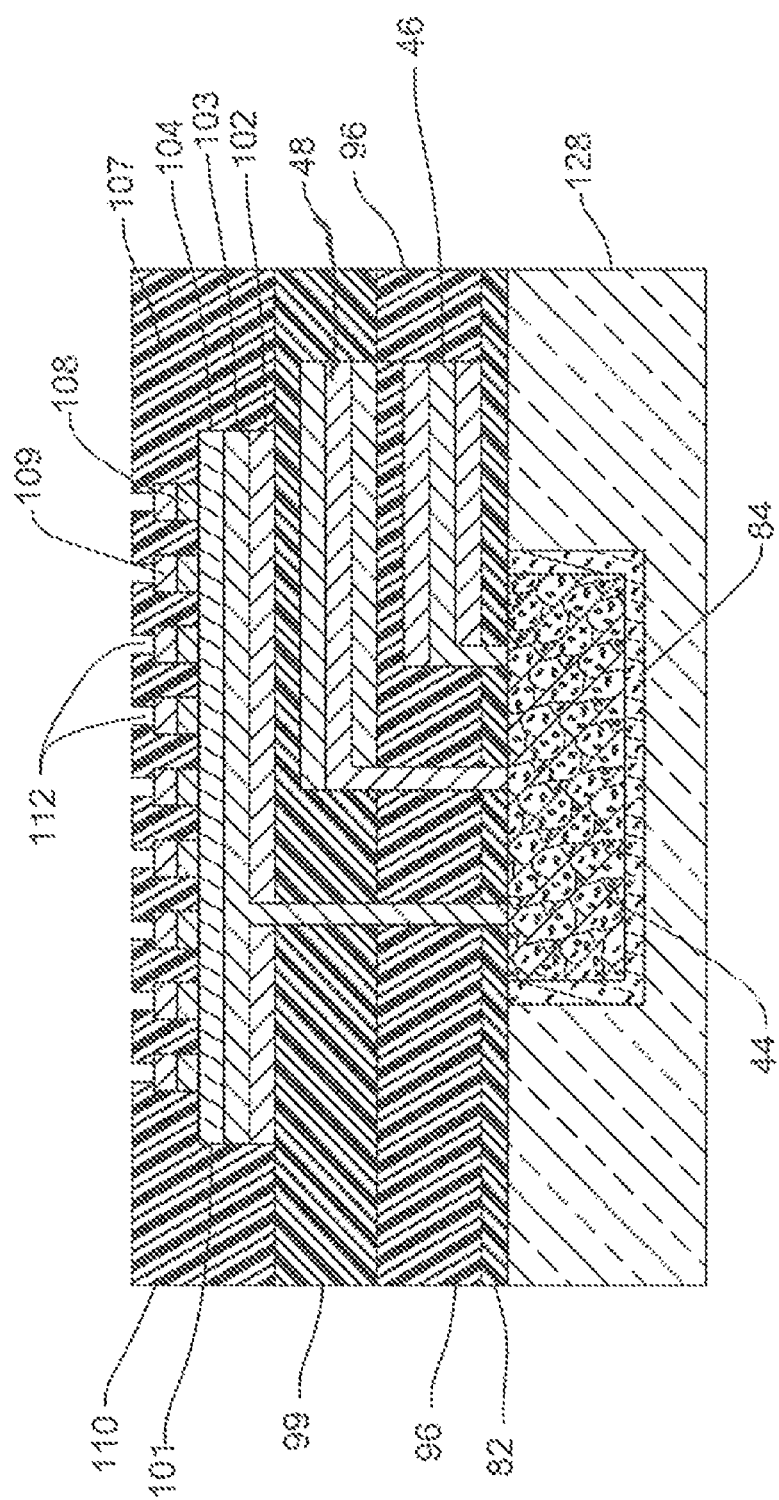

Once the buttons are formed over the electrodes, outer insulating layer 110, is formed over the electrodes. Insulating layer 110, like insulating layers 82, 92, 96 and 99, is a parylene coating. Initially, the parylene forming layer 110 is applied to the whole of the assembly to cover the exposed surfaces of insulating layer 99 as well as the electrodes 42, including the buttons. The parylene forming the portions of insulting layer 110 that extend over insulating layer 99 generally has a thickness of 10 microns or less. While not apparent in the drawings, this thickness is relatively constant, even for the sections of layer 110 disposed over the electrodes 42. Portions of this parylene are selectively removed to forming openings 112 as seen in FIG. 24. In this process, the openings 112 are formed so as to have cross sectional areas that are slightly less than that of the underlying buttons. In other words, the parylene forming outer insulating layer 110 extends around the outer perimeters of the electrode buttons 107. Generally, each opening 112 is formed so as to expose at least 50% of the face of the underlying button 107.

Fabrication of the sub-assembly consisting of the electrodes 42, the control modules 44, conductors 46 and 48 and multiple insulating layers concludes with the separation of the sub-assembly from silicon wafer 128. In one method of this invention, this process is performed by TMAH so as to etch away the silicon forming wafer 128. As seen by reference to FIG. 25, this leaves encased control modules 44 suspended below the laminate structure consisting of the conductors, the insulating layers and the electrodes. This laminate structure can be considered a laminate sheet of insulating material. The control modules 44 are suspended from one side of the sheet, the electrodes 42 are disposed an opposed side of the sheet and the conductors and vias extend through the sheet.

Figure 25:
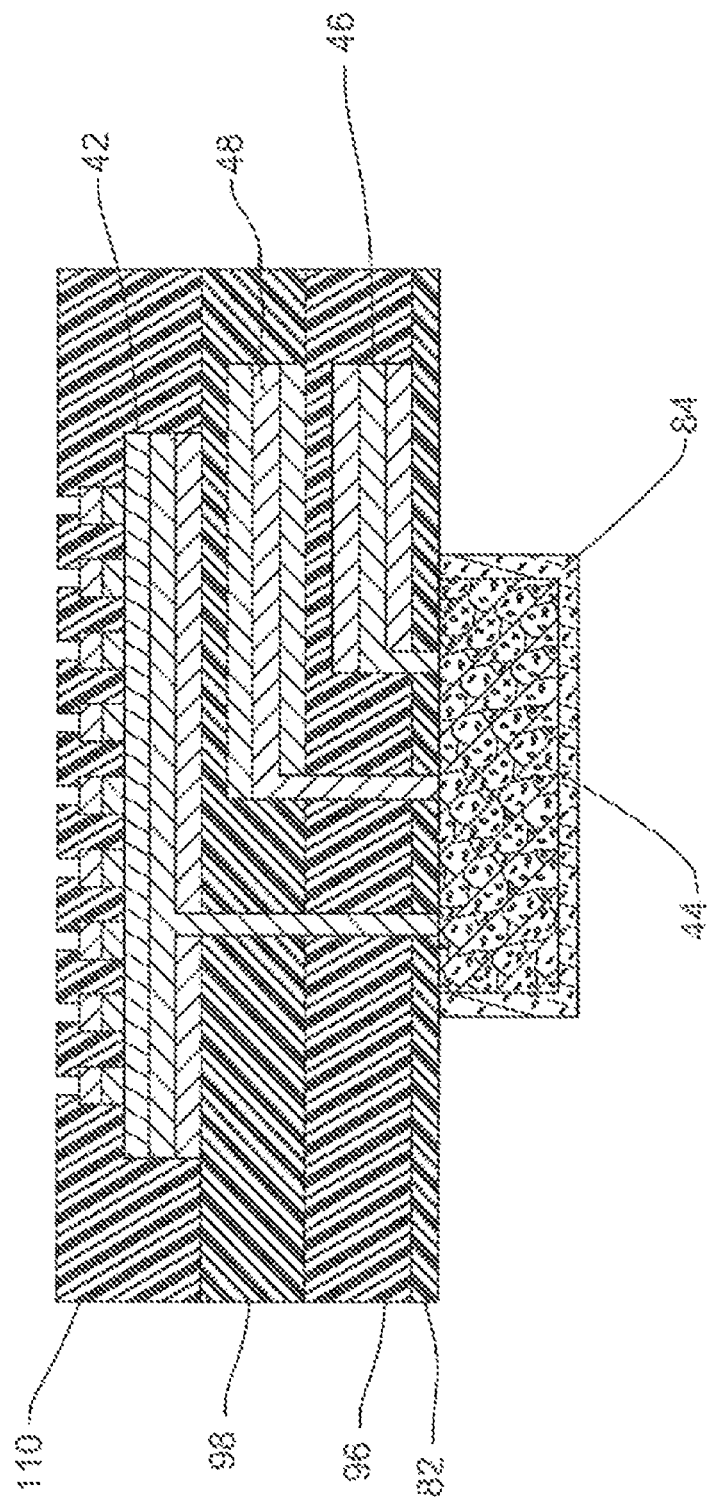

In FIG. 25, only a single electrode 42, a single control module 44 a single pair of conductors 46 and 48 are shown connected to the layers of insulating material. It should be understood that this assembly includes the plural electrodes 42, control modules, conductors 46 and 48 and bus 118 of the electrode array 40.

As part of the presently described method of assembly of this invention, the carrier 80 is prepared to receive the electrode-control module-conductor assembly. This process begins with the basic formation of the carrier which is now described by initial reference to FIGS. 26 and 26A. In the initial steps of the carrier-formation process, a section of a coupon 182 is shaped to define the carrier 80. The coupon 182 is a sheet of the carrier-forming material. In one version of the invention coupon 182 is a sheet of Nitinol that has a thickness of 50 microns. In this process, portions of the coupon 182 are selectively removed to define a set of slots 184 in the coupon that essentially define the whole of the outer perimeter of the carrier 80. Slots 186 and openings 198 are also formed in the coupon so as to define the features of the carrier 80. These features include bridges 188, 190 and 192, that correspond to assembly bridges 58, 60 and 62, respectively. Other features formed in this step are tabs 194 and beams 196 that correspond to assembly tabs 64 and beams 66, respectively. In the Figures, openings 198 are the openings between the adjacent carrier beams 196 that separate the adjacent rows of carrier tabs 194.

Another internal carrier feature formed in this processes are the windows 81 that extend through the carrier-forming section of the coupon 182. Each window 81 is formed so as to be in a location in the carrier 80 in which one of the control modules 44 is mounted. In the illustrated version of the invention, a window 81 is formed in each one of the carrier tabs 194. For reasons apparent below, each window 81 subtends an area that is slightly greater than the area of the occupied by the control module 44 that is to be seated in the window. In one version of the invention, each window 81 is formed so as to allow a separation of approximately 25 microns between the outer surface of the control module shell 84 and the adjacent inner surface of the coupon/carrier section that defines the window. This separation extends around the whole of the perimeter of the shell 84.

In versions of the invention wherein the carrier 80 is formed from Nitinol, these carrier defined features are formed by selectively etching away section of a Nitinol coupon 182. This process is performed by chemical etching.

As mentioned above in the above process, the slots 184 that are formed in the coupon 182 to define the carrier 80 are not formed to completely define the carrier, and therefore completely separate the carrier from the surrounding portion of the coupon. Instead, the coupon 182 is shaped so that small tabs 204 separate the slots 184 so as to connect the carrier-forming section of the coupon with the rest of the coupon 182. In the illustrated version of the invention, two tabs 204 connect the carrier forming section of the coupon with the surrounding section of the coupon. The tabs 204 are located at the opposed longitudinally ends of the carrier forming section of the coupon 182.

In some versions of the invention, the coupon is prepared for the subsequent manufacturing steps by forming the tabs 204 so that the tabs 204 have a thickness that is less than the thickness of the rest of the coupon 182. This process may be performed by an etching process on the sections of the coupon in which the tabs 204 are to be formed so as to only partially remove the material form the forming the coupon 182. In some versions of this invention, this process of partially etching sections of the coupon 182 to form the tabs 204 is performed prior to the step of etching other sections of the coupon to form the carrier defining slots 184 and 186 and openings 198.

While not illustrated, after the carrier 80 is formed on the coupon 182 the carrier may be shaped to develop a shape that is non-planar with respect to the surrounding sections of the coupon 182. For example the carrier of FIGS. 26 and 26A may be bent so as to have arcuate curvature that is perpendicular to the longitudinal axis of the carrier 80. If the carrier 80 is so bent, the lateral side edges of the carrier would thus be above or below the plane of the page on which the carrier of FIG. 26 is presented.

The method of shaping the carrier 80 is a function of the material from which the carrier/coupon is formed. For example, if the carrier/coupon is formed from Nitinol, this shaping may be performed by placing the coupon in a mold in which the carrier is bent appropriately while simultaneously heating the coupon. Under heat, the carrier-defining section of the coupon would develop the desired shape.

FIG. 27 illustrates a longitudinal section through a portion the carrier-defining section of the coupon. Shown in FIG. 27 and subsequent FIGS. 28 and 31-33 is a longitudinal slice through one of the carrier tabs 194, the beams 196 on either side of the tab and a window 81 in the tab.

Once the coupon 182 is formed to define the carrier 80, parylene is coated to the surfaces of the coupon, including the surfaces of the carrier. In FIG. 28 the parylene is shown on the top and bottom faces of the tab 194 and the surfaces of the tab 194 that define window 81. Parylene is also shown on the opposed top and bottom surfaces of the beams 196 and the side surface of the beams 196 directed away from the adjacent tab 194. This parylene is called out as layer 203. Parylene is not shown on the opposed adjacent surfaces of the tab 194 and beams 196 that define the slots 186 between the tab and beams. This omission is for only for ease of illustration. Parylene covers these opposed surfaces. These parylene coatings do not close the gaps between the carrier tabs 194 and bridges 196. As part of this coating process, the parylene is also coated on the sections of the coupon on that do not define the carrier 80.

The parylene-coated coupon 182 is then bonded to a rigid substrate 206 now described with respect to FIG. 29. In one version of the invention, substrate 206 is a silicon wafer. Prior to the carrier bonding process, a layer of silicon dioxide 208 is formed on the outer surface of substrate 206. Silicon dioxide layer 208 serves as a sacrificial release layer. A coating of parylene 210, seen in FIG. 30, is applied to the outer surface of the silicon dioxide layer 208.

Figure 31:
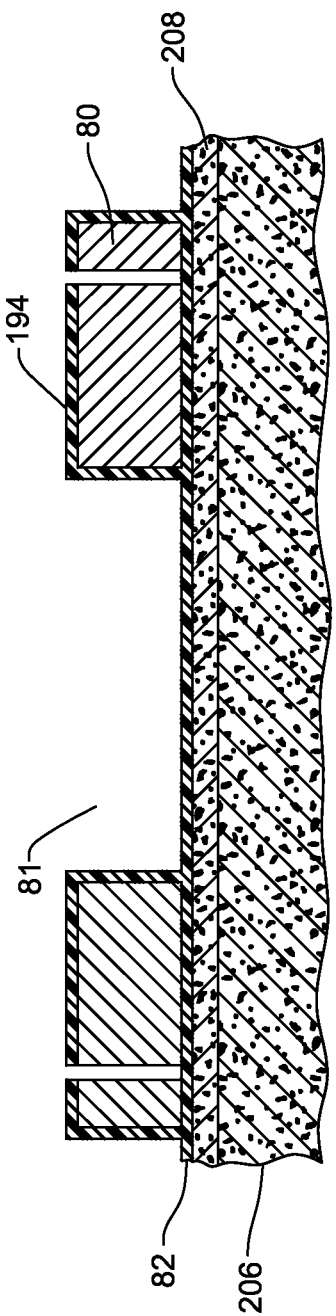
FIGS. 31 and 32 depict how the carrier, once bonded to the substrate, is prepared to receive the electrode-control module-conductor sub-assembly.

FIG. 31 illustrates the bonding of the coupon 182 to the substrate 206. More particularly, in this step, the parylene layer 203 on one the faces of the coupon 182 is bonded to the parylene 210 disposed over the silicon dioxide layer 208. These two parylene layers merge into a single layer that becomes the passive side insulating layer 82 of the electrode array assembly 40. Accordingly, in FIGS. 31-36 this layer is identified as the passive side insulating layer 82.

As described above, some assemblies of this invention may have a carrier 80 that has a non-planar shape. In these versions of the invention, as consequence of the bonding of the carrier-defining coupon 182 to the substrate 206, the carrier 80 is temporarily flexed back into the shape it which the carrier is coplanar with the rest of the coupon 182.

Figure 32:
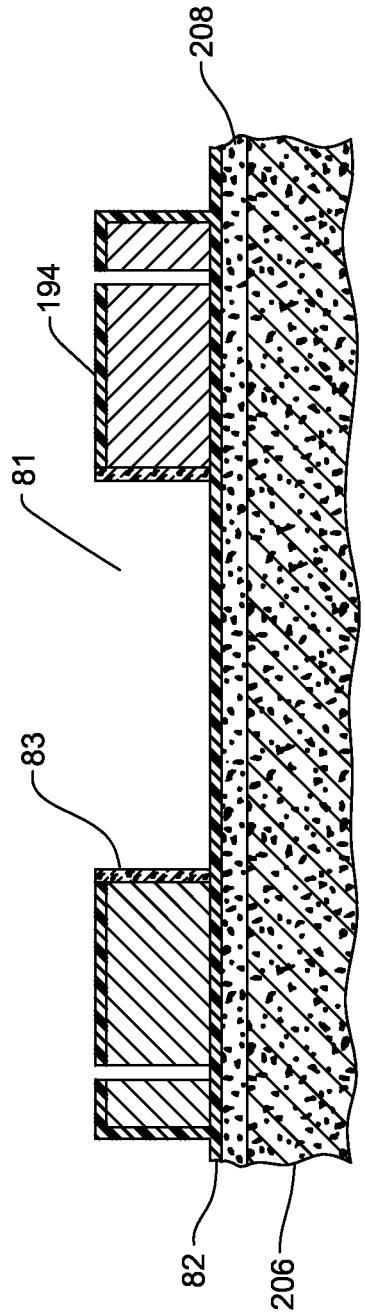

Once the carrier-containing coupon 182 is bonded to the substrate 206, the parylene around the perimeters of the carrier windows 81 is removed, step not shown. The removal of this parylene is performed by reactive ion etching. Once the parylene is removed from around the carrier windows 81, the frame 83 is formed around the surfaces of the carrier that define the windows 81 as seen in FIG. 32 In one version of the invention, the frame 83 is formed by applying a layer of silicon dioxide to the window-defining surfaces using an oxidative deposition process. Alternatively, frame 83 is formed from a polydimethyal silioxane silicon. This type of frame 83 may be applied using an adhesive bonding process.

Figure 33:
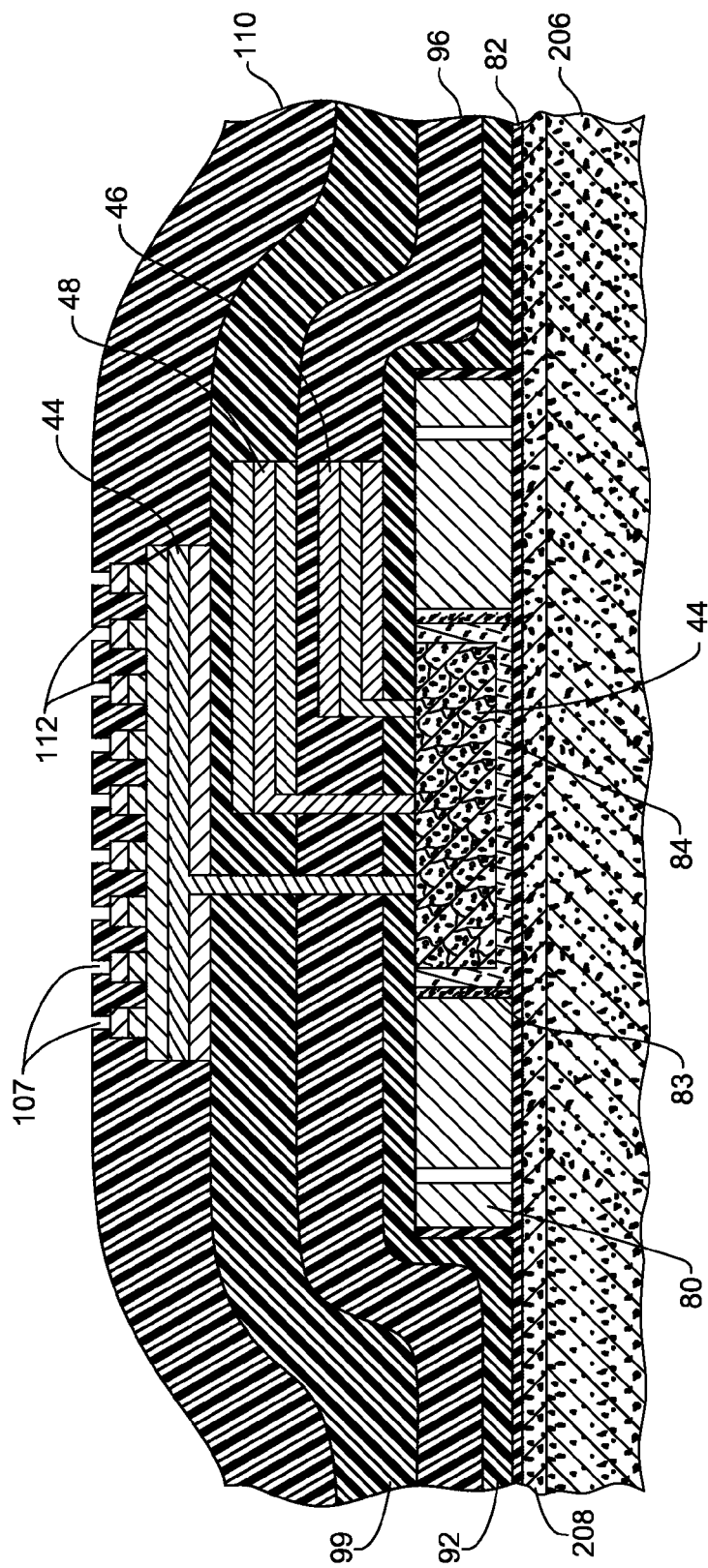
FIG. 33 depicts how the seating of the electrode-control module-conductor assembly on the carrier.

Assembly of electrode array assembly 40 continues with the seating and mating of the electrode-control module-conductor assembly to the coupon 182 as represented by FIG. 33. In this process step, the sub-assembly including the electrodes, the control modules and the conductors is disposed over the carrier-containing coupon 182 so that the shell-encased control modules 44 seat in the carrier windows 81. In this mating process, the parylene of intermediate insulating layer 92 (FIG. 8) of the electrode-control module-conductor assembly is bonded to the exposed parylene layer 203 of the carrier-containing coupon. This parylene-to-parylene bond is what holds the electrode-control module-conductor sub-assembly to the carrier 80. The two parylene layers 92 and 203 become a single parylene layer. Accordingly, in FIGS. 33-37, these layers are identified as the bottom most intermediate insulating layer, layer 92.

In FIG. 33, insulating layers 82, 92, 96, 99 and 110 are shown as extending across the openings 198 that separates the carrier tab 194 from the adjacent beams 196. As discussed above the parylene forming these layer 82, 92, 96, 99 and 110 is applied so as to extend over a surface area that is larger than that of the electrode array 40 under fabrication. Consequently, as seen in FIG. 33, the insulating layers formed by the parylene extends beyond the perimeter of the carrier tabs 104. These insulating layers extend across the gaps between the carrier tabs 194 and the adjacent carrier beams 196. These insulating layers also extend over the carrier windows 198 between the beams 194. Owing to the flexible nature of the parylene, within the carrier openings 198 the parylene forming the passive side insulating layer 82 bonds with the parylene forming the bottommost intermediate insulating layer 92. This parylene-to-parylene bonding is performed under at least a partial vacuum. Consequently, as a result of this process the parylene of layers 92, 96, 99 and 110 collapse over the side edges of the carrier 80. The parylene of layer 92 bonds to the parylene of layer 82. Thus, each membrane 70 is formed by the laminate structure of the insulating layers 82, 92, 96, 99 and 110. Similarly, adjacent the outer edges of the carrier bridges 188 and 192, the parylene layers extends between the longitudinally adjacent carrier tabs 194. In this area between the carrier tabs 194 the parylene forming insulating layers 82 and 92 again bond. Each membrane 72 thus similarly consists of a laminate comprising insulating layers 82, 92, 96, 99 and 110.

Electrode array assembly 40 is now removed from substrate 206. This process begins with the removal of the parylene layers 82, 92, 96, 99 and 110 that extend over carrier slots 184 and 186. The removal of the parylene above and below the carrier slots 186 allows array tabs 64 and beams 66 to flex relative to each other. A reactive ion etch process, an oxygen plasma etch process, can be used to remove these sections of parylene. As a consequence of this etching process, as seen in FIG. 34, tabs 204 are exposed.

The electrode array assembly removal process continues with the severing of the carrier from the surrounding section of the coupon 182. Typically this process involves the removal of tabs 204. In versions of the invention wherein the carrier-defining coupon 182 is formed from Nitinol, tabs 204 are removed by using a mixture of $HF_3$ and $HNO_3$ to etch away the Nitinol forming the tabs. As a consequence of this process, a small remainder section of each tab, identified as crest 212 in FIG. 35 projects outwardly from perimeter of the carrier 80 (one crest shown). A crest also extends outwardly from the surrounding coupon 182. Since that crest is not relevant to this invention, it is not illustrated. Another reactive ion etching process may then be performed to remove the parylene of insulating layer 82 that was previously covered by the tabs.

Once the tabs 204 are removed, a layer of parylene is deposited over the assembly. This layer is approximately 1 micron thick. In FIG. 36, this layer is only illustrated as layer 216 disposed over the sides of the of the carrier 80. Thus, this parylene layer 216 covers the exposed side edges of the frame 80 including the crests 212. While not illustrated, it should be understood that parylene layer 216 also extend over the exposed face parylene layer 110. Once layer 216 is applied, a reactive ion etching process may be used to remove portions of the parylene forming layer 216 so as ensure openings 112 remain open.

The silicon dioxide layer 208 between substrate 206 and the passive side insulating layer is removed. This process may be performed by etching away the silicon dioxide layer 208 using a chemical etch process. As seen by reference to FIG. 37 as a consequence of this etching process the section of the silicon dioxide material disposed under the sections of the coupon 182 that do not function as the carrier are also removed.

Once the silicon dioxide layer is removed from underneath the electrode array assembly 40, the electrode array 40 is no longer connected to either the coupon 182 or the substrate 206. The array 40 is lifted away from the coupon and substrate 206 for any further processing and testing that is not part of this invention.

III. Alternative Method of Assembly

An alternative method of assembling the electrode array assembly 40*a* (FIG. 49) of this invention can start with the formation of the coupon-defining carrier 182 previously described with reference to FIGS. 26, 26A and 27. In this version of the invention, the coupon 182 may have a thickness that is typically no more than 5 microns greater than the thickness of the control module 44. Once the coupon 182 is properly shaped, the carrier-forming section of the coupon may be itself shaped so this section of the carrier acquires the desired non-planar shape of the end assembly 40. The surface of the carrier 182 opposite the surface on which the electrodes 42 are to be disposed is then coated with parylene, step not illustrated. During the application of this parylene layer, the parylene is applied so as to coat the side surfaces of the carrier 80

The coupon-defining carrier 182 is then bonded to the rigid substrate 206. As previously described with respect to FIGS. 29 and 30, substrate 206 is prepared for this bonding process by first applying silicon dioxide layer 208 over the substrate 206. Then, parylene layer 210 is coated over silicon dioxide layer 208.

Figure 38:
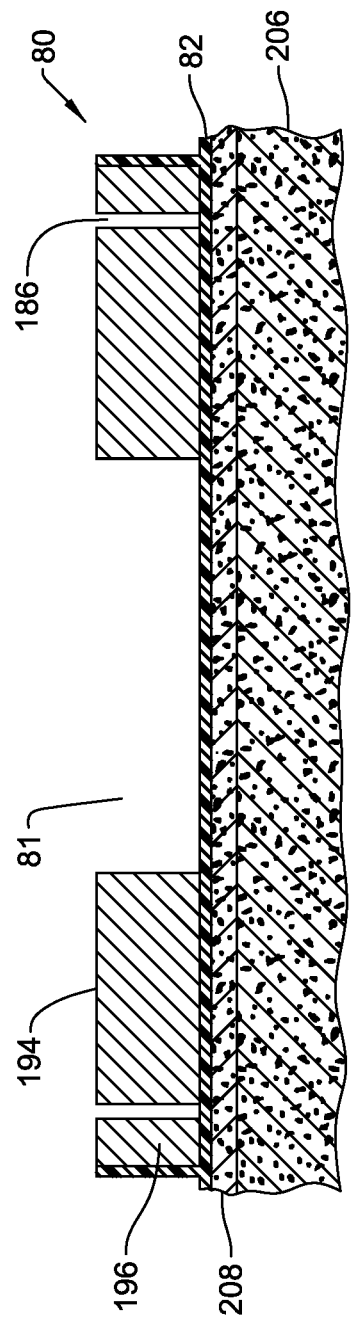
FIGS. 38-48 are a sequence of cross sectional views that depict an alternative process for assembling an electrode array of this invention.

FIG. 38 represents the bonding of the carrier-defining coupon 182 to the rigid substrate 206. If the carrier 80 was, in the early step, shaped, as a consequence of this process, the carrier-forming section of the coupon 182 is flexed back into the plane of the coupon 182. In FIG. 38 and subsequent FIGS. 39-48, the two parylene layers 203 and 210 bonded together are identified as their final form in the assembled array, passive side insulating layer 82. The layer of parylene disposed over the side surfaces of the carrier 80 is considered part of the passive side insulating layer 82.

Figure 39:
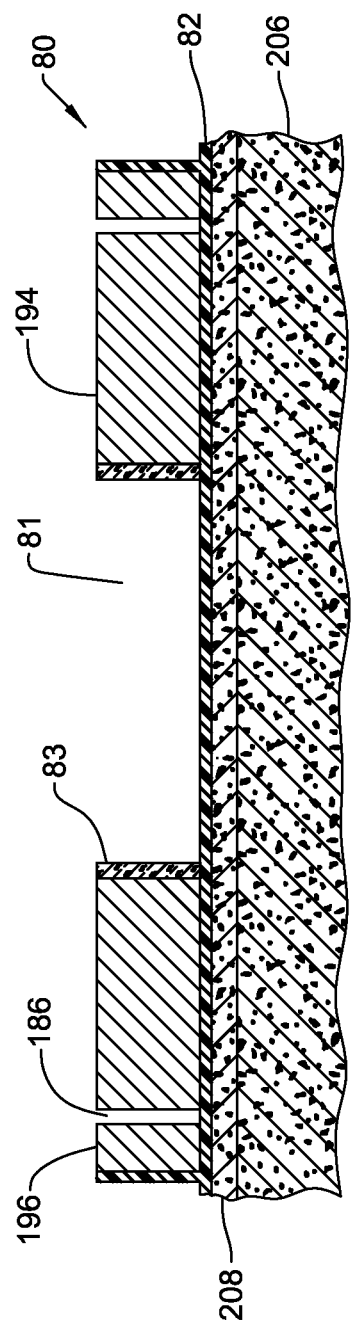

The next step in this method of assembly 40 fabrication of this invention, is, as represented by FIG. 39, the formation of the electrically insulating frame 83. Frame 83 may be formed from the material used to form the frame and using the processes described with respect to FIG. 32.

Figure 40:
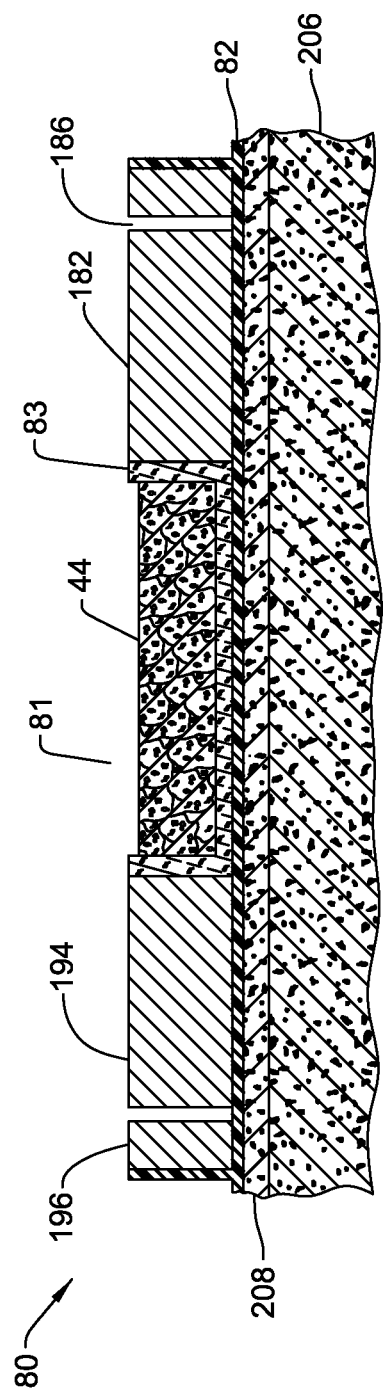

Once frame 83 is formed, in this method of assembling array 40a, control module 44 is seated in the opening defined by the frame 83 as depicted illustrated with respect to FIG. 40. In FIG. 40, control module 44 is shown not encased in a shell. In a variation of this method of assembly of the invention, prior to the seating of the control module 44 in the frame 83, the control module is at least partially encased in a biocompatible shell. For example, the shell may be formed from silicon. In versions of the invention in which the control module is so encased in shell, the coupon 182 from which the carrier 80 is formed has a thickness that is typically no more than 5 microns greater than the combined top-to-bottom thickness of the control module and the shell. Thus, at this stage of the assembly process the top of the control module 44 may be below the surrounding top surface of the carrier-defining coupon 182.

Figure 41:
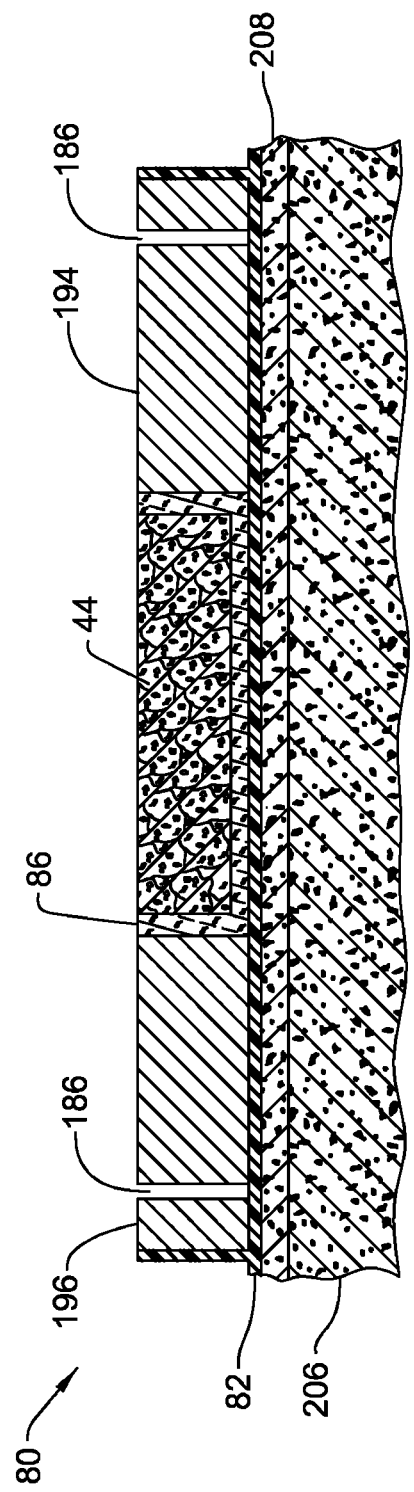

Using a mechanical lapping process, the top section of the carrier-defining coupon 182 and frame 83 are then removed so that, as depicted by FIG. 41, the top surface of the coupon 182 is coplanar with the exposed top surface of the control module 41.

Figure 42:
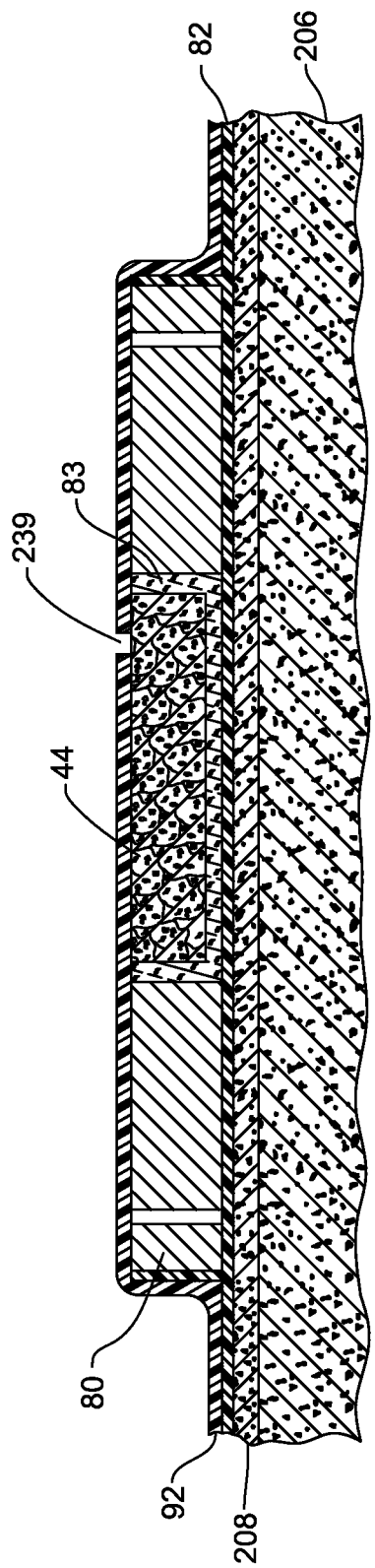

A parylene coating is then applied to the exposed coplanar faces of the control module 44 and the coupon 182, as represented by FIG. 42. This parylene becomes the parylene of intermediate insulating layer 92 and therefore identified as such in FIGS. 42-48. As depicted in FIGS. 42-49 the parylene forming layer 92, as well as the parylene forming insulating layers 96, 99 and 110, extends beyond the top surfaces of the carrier-forming features of the coupon. This parylene extends over slots 184 (not illustrated) and slots 186. This parylene also extends over and into windows 198 formed in the carrier 80. This parylene is bonds to the parylene of the previously applied passive side insulating layer 82. As occurs during the previously described method of manufacture, these multi-layer parylene laminates form the array membranes 70. The While not illustrated, it should be understood from this Detailed Description that parylene forming layer 92 as well as the layers above layer 92 extend between the outermost carrier tabs 194. These multi-layer parylene laminates form the array membranes 72.

Holes 239 (one shown), essentially identical to holes 138 of FIG. 11 are formed in insulating layer 92 to provide access to the underlying control module bond pads 91. The process used to form holes 239 is the same as the process used to form holes 138.

Figure 43:
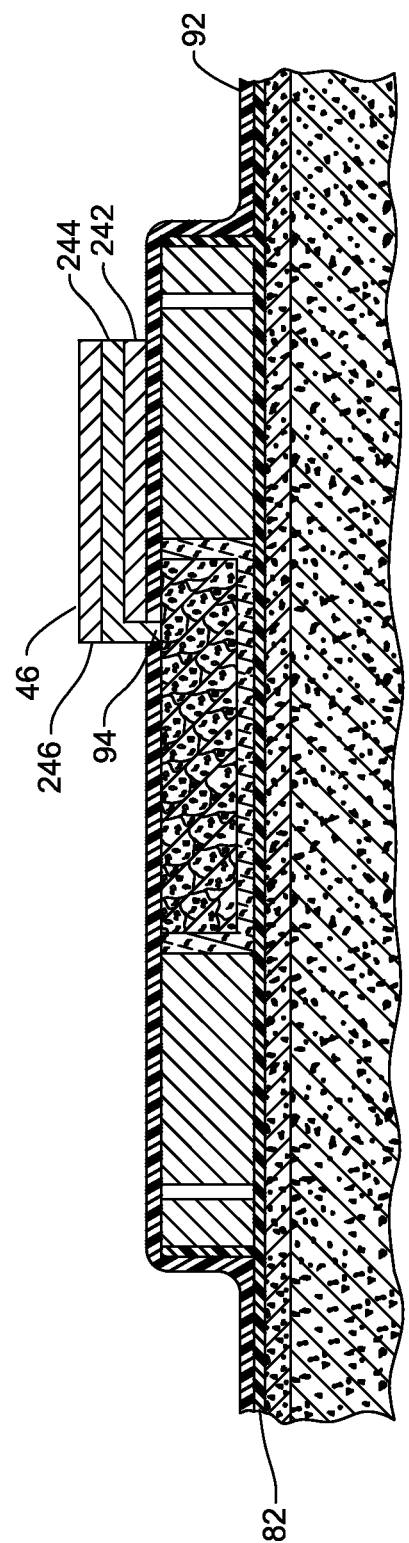

The next series of steps in the assembly of the electrode array 40 according to this method, represented by FIG. 43, is the formation of conductors 46 and associated bus conductor. Conductors 46 are formed using the same processes described with respect to FIGS. 12-15. In FIG. 43 the initial titanium adhesion layer of the conductor is called out as layer 242. The gold layer of conductor 46 is called out as layer 244. The topmost titanium layer is called out as layer 246. The gold applied in the electroplating process used to form the largest section of layer 244 flows into the holes 239 so as to form the vias 94. Formed simultaneously with the conductors 46 is the conductor integral with bus 118 to which the conductors 46 are connected. The same titanium, gold and titanium layers, 242, 244 and 246, respectively that form conductors 46 form the conductor of bus 118.

Figure 44:
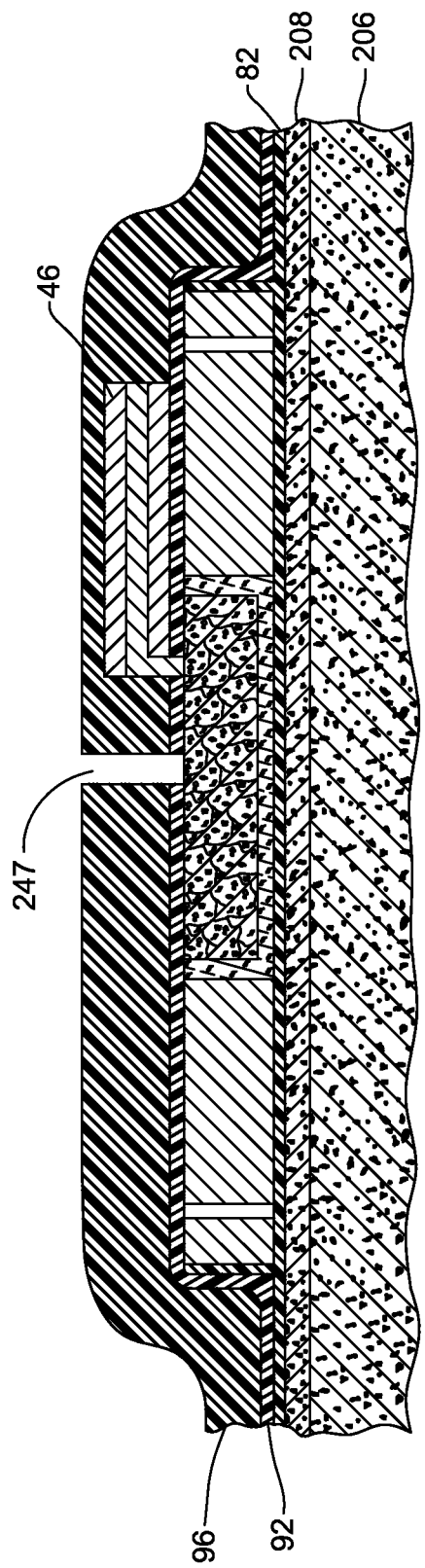

As represented by FIG. 44, a layer of parylene is applied over conductors 46 and the exposed surfaces of the intermediate insulating layer 92 to form intermediate insulating layer 96. Holes 247 (one shown), essential identical to holes 154 (FIG. 17) are formed to extend through insulating layers 92 and 96 to the control module contact pads 91. This step is essentially identical to the step described by reference to FIG. 17 in which the 154 are formed.

Figure 45:
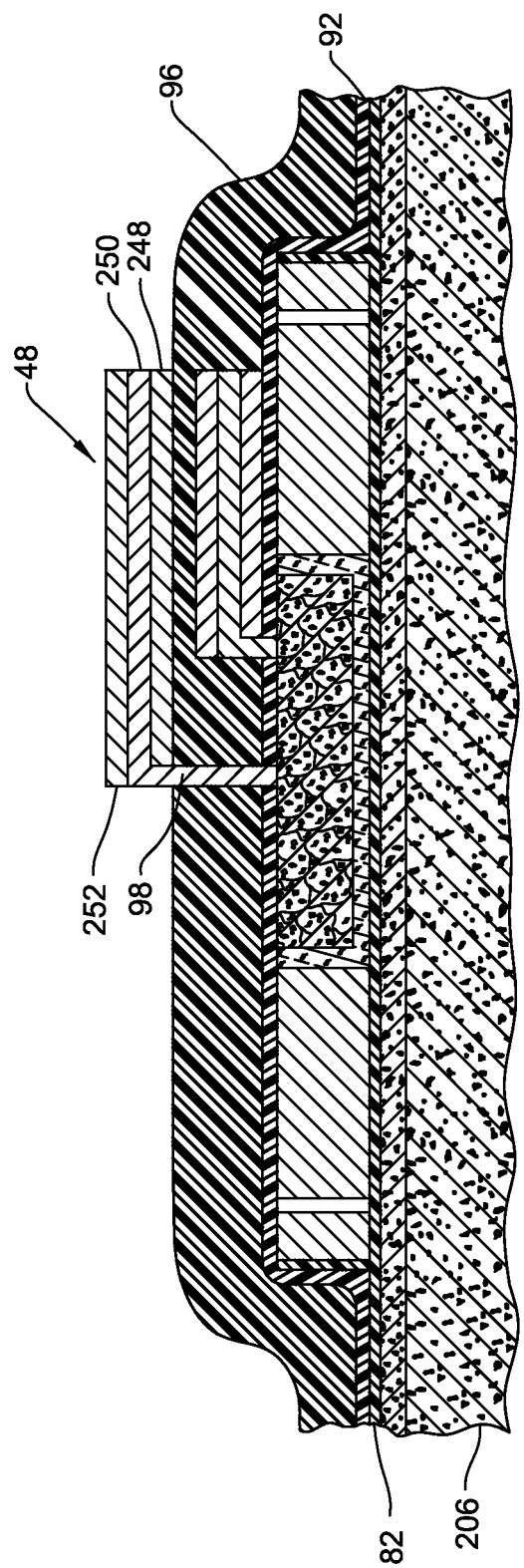

Once the openings are formed in the intermediate insulating layers 92 and 96, conductors 48 are formed. The process steps used to form conductors 48 are the same described with respect to FIGS. 17-19. In FIG. 45 the bottommost titanium layer of conductor 48 is called out as layer 248. The gold intermediate layer is called out as layer 250. The topmost titanium adhesion layer is called out as layer 252. The gold applied by the electroplating to form layer 250 also forms the vias 98.

During the process steps in which conductors 48 are formed, the titanium and gold of layers 248, 250 and 252 is also deposited to from the bus 118 conductor to which conductors 48 are connected. Thus, this conductor is like, conductors 48, disposed over intermediate insulating layer 96.

Figure 46:
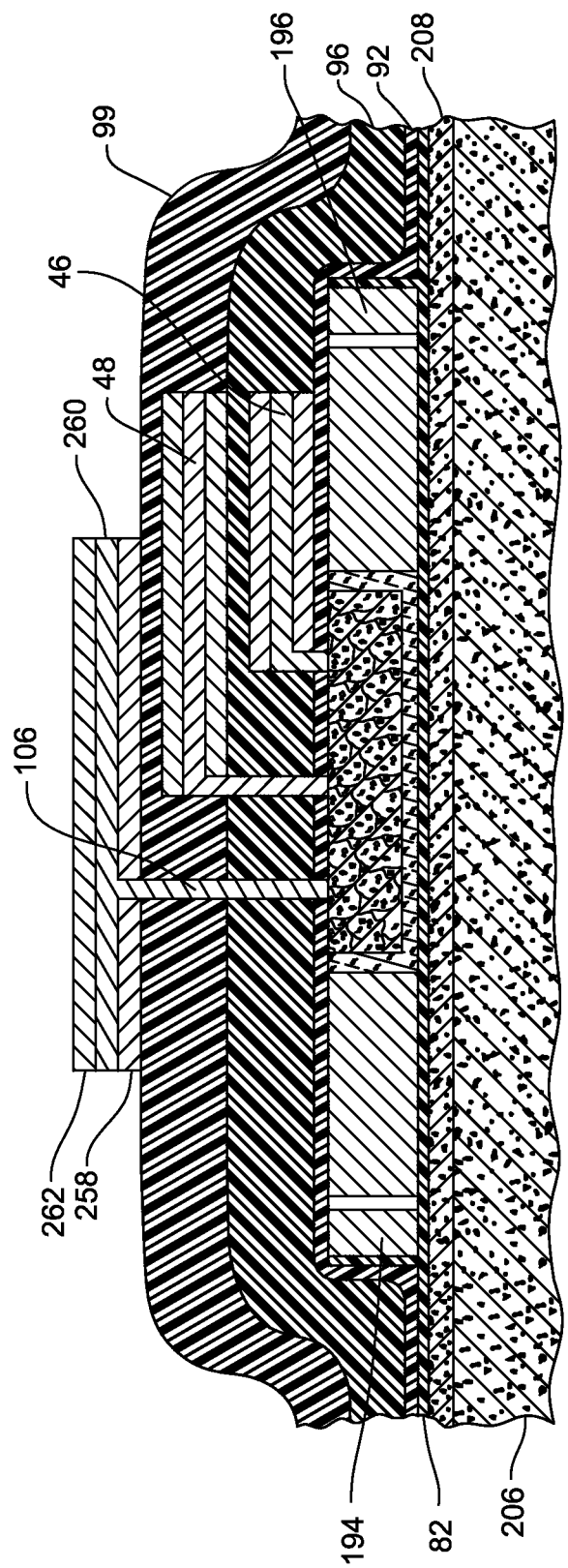

Assembly of electrode array 40 continues with the application of parylene over the exposed surfaces of conductors 48, the bus conductor to which conductors 48 are connected and intermediate insulating layer 96. This parylene, as seen in FIG. 46, forms the intermediate insulating layer 99. Once layer 99 is formed holes (one shown and not identified) are formed in the intermediate insulating layers 92, 96 and 99. These holes extend to bond pads 91 integral with the control modules 44.

Electrodes 42 are then formed on top of intermediate insulating layer 99. The electrodes are formed in process steps analogues to the process steps described with respect to FIGS. 21-23. A titanium adhesion layer is applied to the exposed surface of intermediate insulating layer 99. A gold seed layer is applied over the titanium layer. A mask is applied so as to have openings over where the electrode bond pads are to be located. Gold is added to the exposed sections of the gold seed layer to form the layers 103. A portion of this gold also forms the vias 106. Titanium layers 104 are formed. The mask is removed. The sections of first the gold seed layer and then the underlying titanium adhesion that are not part of the base pads are then removed. Thus, as represented by FIG. 46, the electrode base pad consists of titanium layer 258, gold layer 260 and titanium layer 262.

Figure 47:
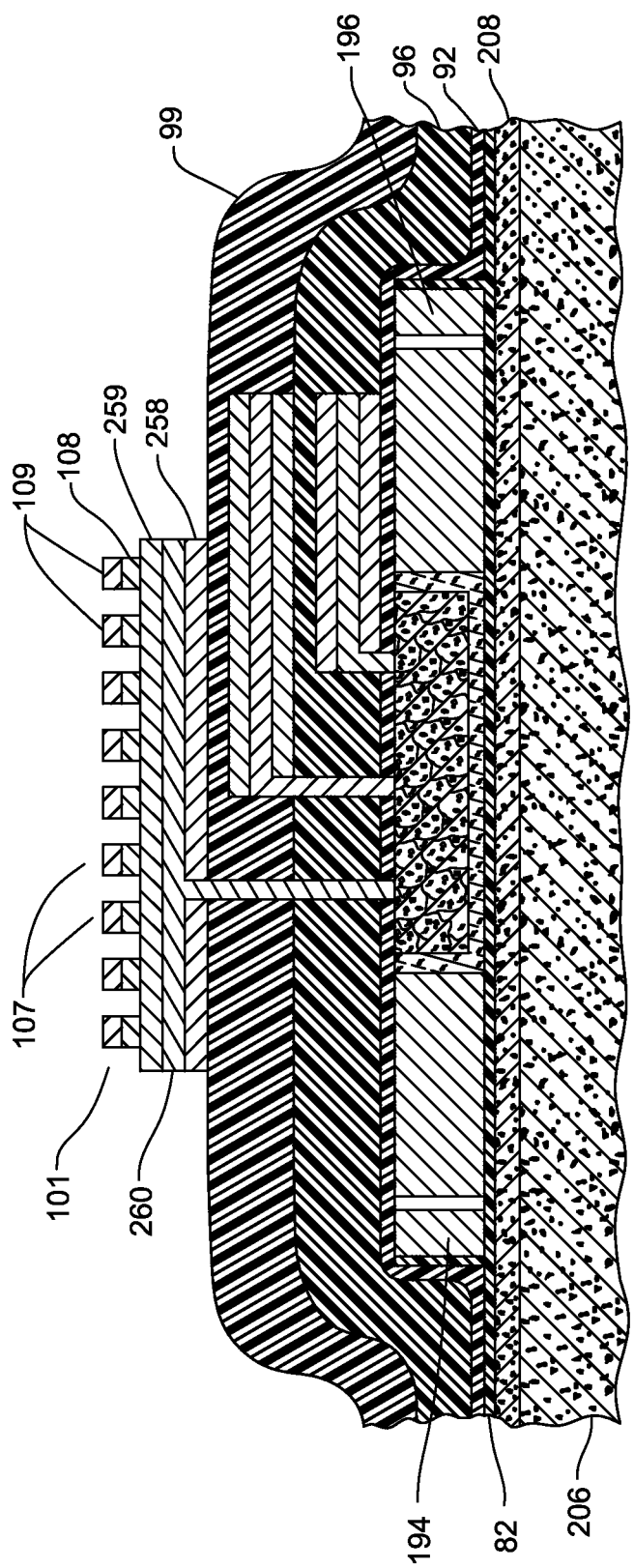

Fabrication of the electrodes 42 continues with the fabrication of the buttons 107. Titanium is initially deposited over the exposed titanium layers 262 of the electrode base pads. Iridium is then deposited over the titanium. In FIG. 47, as in FIG. 2, these layers are called out as titanium layers 108 and iridium layers 109.

Figure 48:
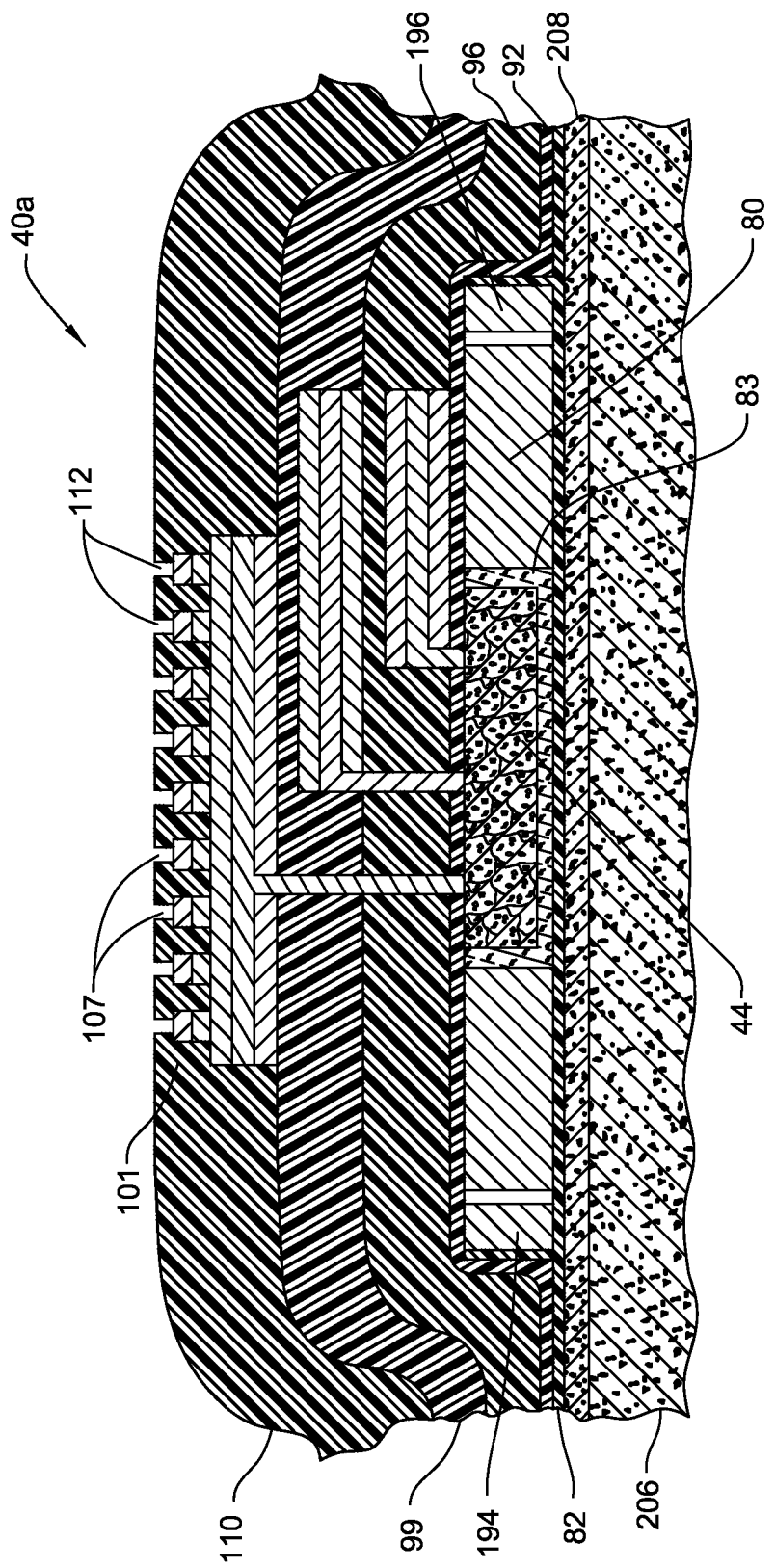

Once the buttons 107 are formed, as represented parylene is applied to the exposed surfaces of the electrodes 42 and the intermediate insulating layer 99 to form the outer insulating layer 110, as represented by FIG. 48. Portions of the insulating layer 110 are removed over electrode buttons 107 to provide the openings 112 through which the buttons are exposed to the tissue.

The essentially completely assembled electrode array 40*a* is then removed from the coupon 182 and substrate 206. The process steps used to accomplish these separations are identical to those described with respect to FIGS. 34-37. These process steps include the steps of selectively removing the parylene so as to uncover the slits 184 and 186 around and in the carrier. Tabs 204 are removed. A layer 216 of parylene is applied so as to cover the exposed surfaces of the carrier. Sacrificial layer 208 is removed to allow the array 40*a* to be lifted of the substrate 204.

In this method of assembling the electrode array 40, the control modules 44 are seated in the carrier during an initial step of assembly process. The application of the insulating layers 92, 96, and 99 over the substrate can be considered the formation of a flexible sheet of insulating material over the substrate. The insulating and conductive layers that collectively define the array 40 electrodes, conductors and vias are formed on the carrier. Thus, in this version of the invention the process steps associated with having to bond an electrode and conductor sub assembly to the carrier are eliminated.

IV. Alternative Electrode Array

Figure 49:
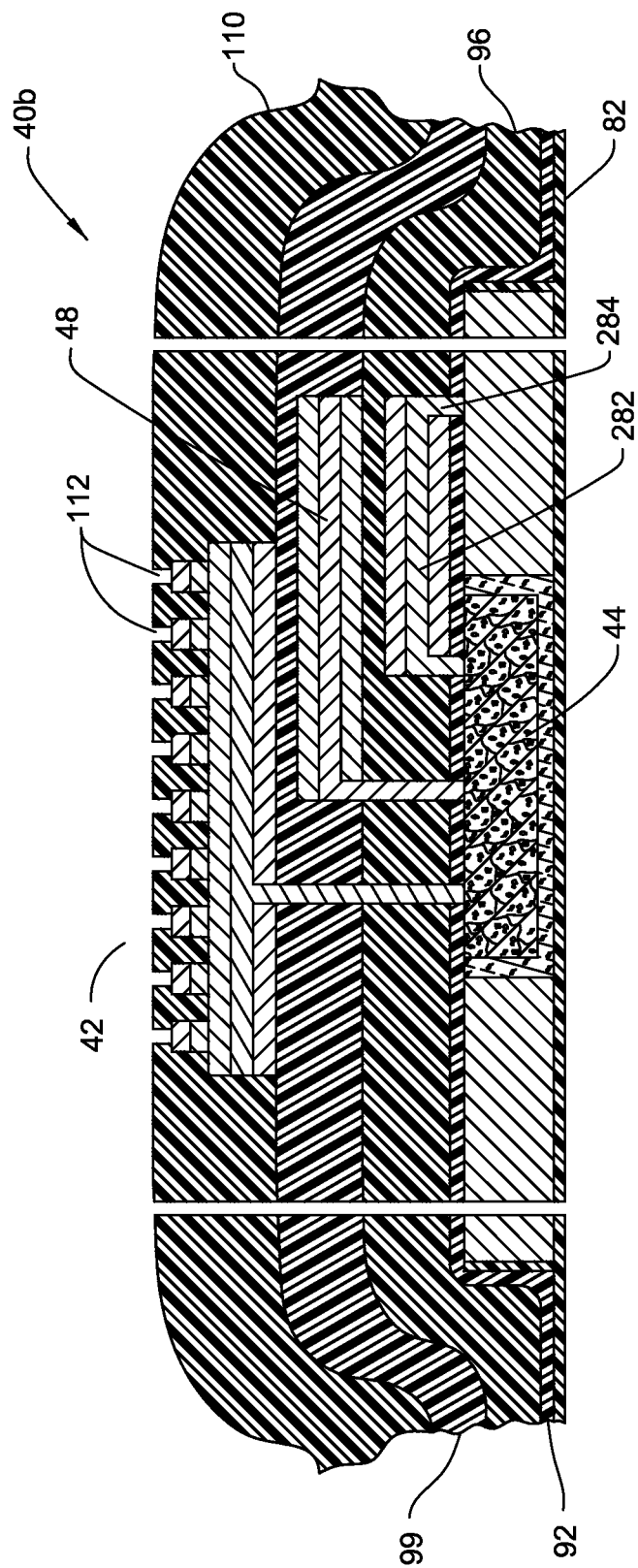
FIG. 49 is a cross sectional view of a single electrode and control module of an alternative electrode array of this invention.

FIG. 49 illustrates in cross section a portion of an alternative electrode array 40*b* of this invention. Electrode array 40*b* of this invention includes the same electrode, control module 44 and carrier 80 of the previously described versions of this invention. Array 40*b* includes the previously described conductor 48 and insulating layers 82, 92, 96, 99, 110 and 216 (layer 216 not illustrated.)

Instead of the previously described conductors 46, array 40*b* includes a conductor 282. Conductor 282 extends from a bond pad 91 integral with the control module 44 over a section of intermediate insulating layer 92 to a location over the carrier. In FIG. 49, conductor 282 is shown extending over the carrier tab 194 in which the control module 44 with which the conductor 282 is seated. A via 284, which extends through intermediate insulating layer 92, connects the end of conductor 282 to the carrier 80.

Figure 50:
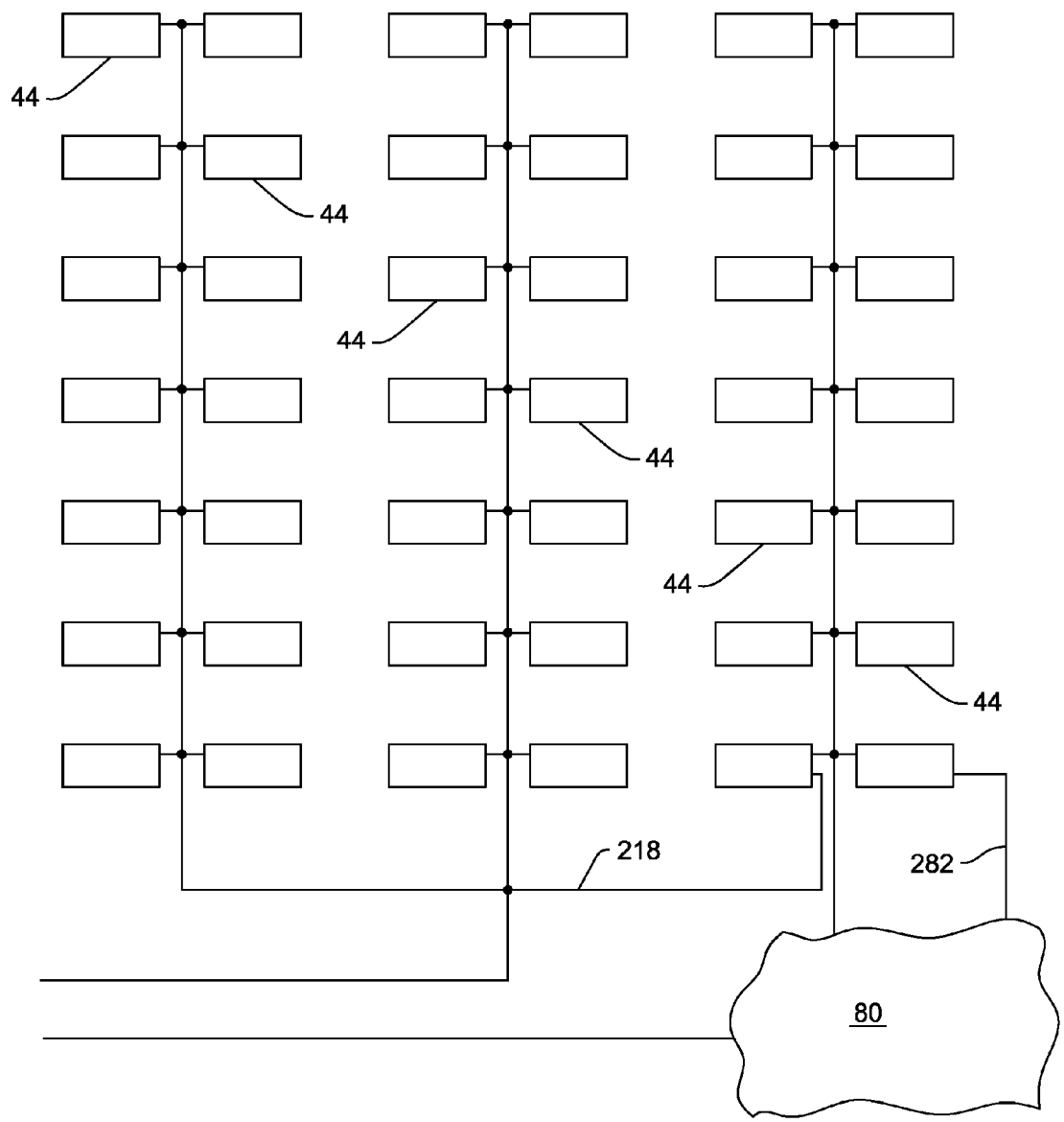
FIG. 50 is a block diagram of how signals are distributed to the control modules of the electrode array of FIG. 50.

In this version of the invention, the carrier 80, which is formed from conductive material, functions as the common ground plane for the plurality of control modules 44. Consequently, as seen in FIG. 50, array 40*b* is constructed so that a one-wire bus 288 functions as the conduit over which power and control signals are transmitted to the plurality of control modules 44.

IV. Alternative Embodiments

It should be appreciated that the foregoing is directed to specific constructions and specific methods of assembly of this invention. Alternative construction as well as alternative methods of manufacture of this invention are possible.

For example, there is no requirement that in all versions of the invention that each electrode 42 have its own control module. In some versions of the invention, it may only be necessary to provide the electrode array with a single carrier-embedded control module. Alternatively, one or more control modules may be able to serve as the components through which current is sourced to or sunk from plural electrodes. It should therefore be appreciated that there is no requirement that in each version of the invention, the control module that sources current to or which current is sunk from an electrode be mounted to the carrier so as to subtend the area occupied by the electrode. Thus it is contemplated that in some versions of the invention, the control modules may be mounted in locations in the carrier that are spaced away from the locations over which the electrodes are formed.

Also, it may be necessary to provide an electrode array of this invention with one or more control circuits that, owing to their design, cannot be assembled into carrier-implantable control modules. In these versions of the invention one or more of these additional control modules may be mounted to either the active or passive side of the electrode array.

Similarly, the functions of the embedded control modules are not limited to modules that source/sink current to the electrodes. Some control modules may contain components useful for processing signals received by the electrodes. Thus when a particular electrode does not function as a current source or sink, these components internal to the control module process the potential measured by the electrode so these potential measurements can be further processed by other components. Whether or not a specific control module contains components to source current and/or sink current and/or process a potential measured by an electrode or electrodes is a function of the specific electrode array. Still other alternative control modules may not include any of these processing components. These control modules may include devices for storing the charge that is used to flow current between the electrodes. Other control modules may include components for providing connections between the electrode array 40 and components off the array.

Likewise, the shapes of the components may be different from what has been described. Thus, while in the described versions of the invention, the electrodes are located on tabs that are separate from the surrounding sections of the carrier, this is not required in all versions of the invention. There is no requirement that in all versions of the invention, the electrodes be arranged in the row by column array. Thus, for some applications of the invention, the electrodes may be arranged in a single column on the carrier.

Similarly, there is no requirement that in all versions of the invention, the control modules be seated in windows that extend completely through the carrier. In some versions of the invention, the carrier may be formed with recesses that do not extend all the way through the carrier. In these versions of the invention, the material forming the passivation frame is applied to the surfaces of the carrier that form the bases of the recesses. Thus, in these versions of the invention, the material forming the passivation frame forms a shell that insulating frame between the die forming control module 44 and the surrounding carrier.

Likewise, there is no requirement that in all versions of the invention, the electrode array 40 be formed from the disclosed components. For example, there is no requirement that in all versions of the invention the carrier be formed from material that is superelastic or even material that is deformable. In some versions of the invention, the carrier can be formed from material that is simply flexible. This is usefully when constructing an electrode array that is to placed against irregularly shaped tissue. In these and other versions of the invention, the carrier therefore may not be formed from metal or other electrically conductive material. Thus, the carrier may formed from a plastic such as silicone or a polyamide. In versions of the invention wherein the carrier is not formed from electrically conductive material, the need to provide an electrical insulating shell and/or frame between the control module and the carrier may be eliminated.

The number of conductors extending to the electrodes 42 and to the embedded control modules 44 should likewise be recognized as illustrative, not limiting. In some versions of the invention, to ensure charging balancing across a single electrode 42 plural vias or other conductors may extend from the control module to that electrode. Likewise, in some versions of the invention only a single conductor or three or more conductors may extend to the embedded control module. For example, in some versions of the invention, one conductor may serve as a common power bus. This bus serves as the conductor over which power, and only power, is distributed to each of the control modules 44. One or more additional conductors function as the bus over which control signals are broadcast to the control modules and data are received back from the control modules.

In the illustrated version of the invention, conductors 46 and 48 that extend to the embedded control module are shown as stacked one below the other. This is likewise understood to be for purposes of illustration and not limiting. In some versions of the invention, if the conductors are positioned on different heights they may not overlap each other. In some versions of the inventions plural conductors that are located at the same height, (that are disposed over the same insulating layer) may extend to one or more common control members.

Likewise, in some versions of the invention, some of the conductors may extend directly to the electrodes. Also, it may be desirable to provide vias that connect the conductors located at different heights, (that are disposed over different insulating layers) with vias. These vias are formed by employing variations of the above described fabrication techniques. Thus, after an insulating layer is formed over a conductor, a hole is formed in the layer so as to terminate over the conductor. The next level conductor is formed over the outer insulating layer. As part of this process of forming this conductor, some of the metal forming the conductor flows into this hole to form a conductor-to-conductor via.

The process steps performed to fabricate an electrode array of this invention likewise may differ from what has been described. Thus, the process steps of the different versions of the invention may be selectively combined. Also, preformed sheets of insulating material and or conductors that are partially or fully shaped to their final forms may be used to form, respectively, one or more of the insulating layers or conductors of the invention.

Similarly, the die forming the control module 44 may not simply be seated in the associated shell. In some versions of the invention, a layer of parylene may be applied to the inner surfaces of the walls of the shell prior to the placement of the die. Once the parylene layer is established, the die is placed in the shell. Given the elastic nature of this parylene layer, the parylene layer functions as shock absorber that reduces the mechanical shock and vibrations to which the control module is exposed. Alternatively, or in addition to the parylene, an adhesive may be applied to the die so as to secure the control module 44 in the shell.

Likewise, an adhesive may be applied to the outer surface of the shells 84. When the shells are seated in the windows 81 of the carrier, this adhesive forms a bond between the shell 84 and the adjacent frame 81 of window-defining surface of the carrier 81.

Therefore, it is the goal of the appended claims to cover all such modifications and variations that come within the true spirit and scope of this invention.

What is claimed is:

1. An electrode array assembly, said assembly comprising:
   a carrier, said carrier formed from material that is flexible and having first and second opposed faces, said carrier formed so as to define at least one recess that extends inwardly from the first face;
   a control module for regulating the operation of or monitoring the signal present at at least one electrode, said control module being disposed in the recess of said carrier;
   a first layer of insulating material disposed over at least the first face of said carrier and said control module, said first layer of insulating material being formed out of material that is electrically insulating and that is more flexible than said carrier, said first layer of electrically insulating material having an outer surface that is spaced from the first face of said carrier;
   a plurality of spaced apart electrodes mounted to said first layer of insulating material so that when the outer surface of said layer is disposed against tissue, said electrodes are in electrical contact with the tissue;
   at least one first conductor disposed in said first layer of insulating material so as to extend across said carrier wherein, at least a portion of said at least one first conductor is contained in said first layer of insulating material so as to be spaced above the first face of said carrier and said at least one first conductor is connected to said control module to function as a conductor over which signals or power are forwarded to or exchanged with said control module; and
   at least one second conductor at least partially contained in said first layer so as to electrically connect said control module to said electrode 2. The electrode array assembly of claim 1, wherein:
   said control module has at least one bond pad across which signals are applied to or output from said control module; and
   a via extends from said bond pad of said control module away from said carrier and said control module through at least a portion of the first layer of insulating material to establish an electrical connection between said control module and said at least one first conductor.

3. The electrode array assembly of claim 1, wherein:
   said control module has at least one bond pad across which signals are applied to or output from a said electrode;
   at least one said electrode is at least partially disposed over said control module; and
   said at least one second conductor is a via that extends from said bond pad of said control module away from said carrier and control module through at least a portion of said first insulating layer to a portion of said electrode disposed over said control module to establish an electrical connection between said control module and said electrode.

4. The electrode array assembly of claim 1, wherein said carrier is formed so that the recess in which said control module is disposed extends between the first and second opposed faces of said carrier.

5. The electrode array assembly of claim 1, wherein:
said carrier is formed so that the recess in which said control module is disposed extends between the first and second opposed faces of said carrier;
said at least one control module has a first face located adjacent the first face of said carrier and a second face located adjacent the second face of said carrier;
a second layer of insulating material is disposed over the second face of said carrier and the second face of said at least one control module, said second layer of insulating material being formed from material that is electrically insulating and that is more flexible than said carrier.

6. The electrode array assembly of claim 1, wherein:
said carrier has sides that extend between the first and second faces of said carrier;
a second layer of insulating material is disposed over the second face of said carrier, said second layer of insulating material being formed from material that is electrically insulating and that is more flexible than said carrier; and
at least one of said first layer of insulating material or said second layer of insulating material extends outwardly of said carrier and is bonded to the other of said second layer of insulating material or said first layer of insulating material so that the sides of said carrier are disposed within at least one of the said first layer of insulating material or said second layer of insulating material.

7. The electrode array assembly of claim 1, wherein at least a portion of said carrier is formed from material that is superelastic.

8. An electrode array assembly, said assembly including:
a carrier, said carrier formed from material that is flexible and having first and second opposed faces, said carrier formed so as to define at least one recess that extends inwardly from the first face;
a control module for regulating the operation of or monitoring the signal present at at least one electrode, said control module disposed in the recess of said carrier;
a first layer of insulating material disposed over at least the first face of said carrier and said control module, said first layer of insulating material being formed out of material that is electrically insulating and that is more flexible than said carrier, said first layer of electrically insulating material having an outer surface that is spaced from the first face of said carrier;
a plurality of spaced apart electrodes mounted to said first layer of insulating material so that when the outer surface of said layer is disposed against tissue, said electrodes are in electrical contact with the tissue;
at least one first via that extends from said control module so as to extend away from the first face of said carrier and through said first layer of insulating material, said at least one first via extending to at least one of said electrodes so as to provide an electrical connection between said control module and said electrode;
at least one conductor disposed in said first layer of insulating material so as to extend across said carrier wherein at least a portion of said at least one conductor is contained in said first layer of insulating material so as to be spaced above the first face of said carrier and said at least one control module, wherein said at least one conductor functions as a conductor over which signals or power are forwarded to or exchanged with said control module; and
at least one second via that extends from said control module so as to extend away from the first face of said carrier and at least partially through said first layer of insulating material to said at least one conductor so as to provide a conductive path between said control module and said at least one conductor.

9. The electrode array of claim 8, wherein:
said at least one electrode is at least partially disposed over said at least one control module; and
said at least one first via extends from said at least one control module to a portion of said at least one electrode disposed over said control module.

10. The electrode array of claim 8, wherein said at least one electrode is at least partially embedded in said first layer of insulating material.

11. The electrode array of claim 8, wherein:
said first layer of insulating material consists of a laminate structure of individual sub-layers of electrically insulating material wherein: a first sub-layer of electrically insulating material is disposed over the first face of said carrier and said at least one control module; and a second sub-layer of electrically insulating material is disposed over the first sub-layer of electrically insulating material
said at least one conductor is disposed between the first and second sub-layers of electrically insulating material;
said at least one second via extends through the first sub-layer of electrically insulating material;
said at least one electrode extends over the second sub-layer of said electrically insulating material so that second sub-layer of electrically insulating material isolates said at least one electrode from said at least one conductor.

12. The electrode array of claim 11, wherein:
said at least one electrode is at least partially disposed over said at least one control module; and
at least a portion of said at least one conductor is contained between the first and second electrically insulting sub-layers so as to be located below said at least one electrode.

13. The electrode array of claim 11, wherein said at least one electrode is at least partially disposed over said at least one control module; and
at least a portion of said conductor is contained between the first and second electrically insulting sub-layers so as to be located above said control module and below said at least one electrode.

14. An electrode array assembly, said assembly comprising:
a carrier, said carrier formed from material that is flexible and having first and second opposed faces, said carrier formed from to have: at least one recess that extends inwardly from the first face; and at least two structural features that are spaced apart from each other;
a control module for regulating the operation of or monitoring the signal present at at least one electrode, said control module disposed in the recess of said carrier;
a first layer of insulating material disposed over at least the first face of said carrier and so as to be located between said carrier and said electrodes, said first layer of insulating material being formed out of material that is electrically insulating and that is more flexible than said carrier, said first layer of electrically insulating material having an outer surface that is spaced from the first face of said carrier and extending between the at least two structural features of said carrier so as to form a flexible membrane that extends between the structural features;
a plurality of spaced apart electrodes that are directed outwardly from said first layer of insulating material so that when the outer surface of said layer is disposed against tissue, said electrodes are in electrical contact with the tissue;

at least one first conductor disposed in said first layer of insulating material so as to extend across said carrier wherein at least a portion of said at least one first conductor is contained in said first layer of insulating material so as to be spaced above the first face of said carrier, wherein said at least one first conductor is connected to said control module and functions as a conductor over which signals or power are forwarded to or exchanged with said control module; and at least one second conductor disposed in said first layer of insulating material that electrically connects said control module to one of said electrodes.

15. The electrode array of claim 14, wherein said at least one second conductor extends through said first layer of insulating material.

16. The electrode array of claim 14, wherein:

said carrier has sides that extend between the first and second faces of said carrier;

a second layer of insulating material is disposed over the second face of said carrier said second layer of insulating material being formed from material that is electrically insulating and that is more flexible than said carrier; and at least one of said first layer of insulating material or said second layer of insulating material extends outwardly of said carrier and is bonded to the other of said second layer of insulating material or said first layer of insulating material so that the sides of said carrier are disposed within at least one of the said first layer of insulating material or said second layer of insulating material.

17. The electrode array of claim 14, wherein:

said carrier is formed so that the spaced apart structural members include: spaced apart bridges; and spaced apart beams that extend between said spaced apart bridges such that a set of spaced apart bridges and spaced apart beams forms an opening in said carrier; and said first layer of insulating material extends between the spaced apart bridges and the spaced apart beams so as to form a flexible membrane that extends over the opening in said carrier.

18. The electrode array of claim 17, wherein at least said beams of said carrier is formed from material that is superelastic.

19. The electrode array of claim 14, wherein:

said at least one control module has a first face located adjacent the first face of said carrier;

said first layer of insulating material is disposed between the first face of said control module and said electrodes; and said at least one second conductor extends from the first face of said control module, away from said carrier and through said first layer of insulating material to said at least one electrode.

20. The electrode array of claim 14, wherein said at least one electrode is at least partially embedded in said first layer of insulating material.

21. The electrode array assembly of claim 14, wherein said at least one second conductor is a via extends from said control module away from said carrier and said control module through at least a portion of the first insulating layer to establish an electrical connection between said control module and said at least one conductor.

22. The electrode array assembly of claim 14, wherein:

at least a portion of one said electrode is disposed over said control module;

said first layer of insulating material is disposed between one side, said carrier and said control module and on an opposed side, said electrodes; and said second conductor extends from said control module through said first layer of insulating material to the portion of said at least one electrode disposed over said control module.

23. The electrode array assembly of claim 14, wherein said first layer of insulating material is disposed over said control module.

* * * * *